United States Patent
Bouchard et al.

[11] Patent Number: 5,959,125
[45] Date of Patent: Sep. 28, 1999

[54] TAXOIDS, PREPARATION THEREOF, AND PHARMACEUTICAL COMPOSITIONS CONTAINING SAME

[75] Inventors: Hervé Bouchard, Thiais; Jean-Dominique Bourzat, Vincennes; Alain Commerçon, Vitry-sur-Seine, all of France

[73] Assignee: Rhone-Poulenc Rorer S.A., Antony, France

[21] Appl. No.: 08/930,561

[22] PCT Filed: Apr. 1, 1996

[86] PCT No.: PCT/FR96/00487

§ 371 Date: Oct. 2, 1997

§ 102(e) Date: Oct. 2, 1997

[87] PCT Pub. No.: WO96/31493

PCT Pub. Date: Oct. 10, 1996

[30] Foreign Application Priority Data

Apr. 3, 1995 [FR] France .................. 95 03868

[51] Int. Cl.⁶ .................................. C07D 305/14
[52] U.S. Cl. ...................... 549/510; 549/511; 514/449
[58] Field of Search .................. 549/510, 511; 514/449

[56] References Cited

U.S. PATENT DOCUMENTS

| | | | |
|---|---|---|---|
| 5,254,580 | 10/1993 | Chen et al. | 514/449 |
| 5,532,388 | 7/1996 | Bouchard et al. | 549/510 |
| 5,550,261 | 8/1996 | Bouchard et al. | 549/510 |
| 5,571,917 | 11/1996 | Bouchard et al. | 544/369 |
| 5,576,450 | 11/1996 | Bouchard et al. | 549/510 |
| 5,580,997 | 12/1996 | Bouchard et al. | 549/510 |
| 5,580,998 | 12/1996 | Bouchard et al. | 549/510 |
| 5,587,493 | 12/1996 | Bouchard et al. | 549/510 |
| 5,599,942 | 2/1997 | Bouchard et al. | 548/215 |

FOREIGN PATENT DOCUMENTS

2698871-A1  6/1994  France .

OTHER PUBLICATIONS

English Abstract of French Patent No. FR 2 698 871–A1, Jun. 10, 1994.

Primary Examiner—Ba K. Trinh
Attorney, Agent, or Firm—Finnegan, Henderson, Farabow, Garrett & Dunner, L.L.P.

[57] ABSTRACT

Novel taxoids of general formula (I), wherein R is a substituted alkyl radical or an alkenyl, alkynyl, cycloalkyl, optionally substituted cycloalkenyl or phenyl radical, or an aromatic 5- or 6-membered heterocyclic radical; and Z is a hydrogen atom or a radical of general formula (II), wherein $R_1$ is an optionally substituted benzoyl, thenoyl or furoyl radical or a radical $R_2$—O—CO, where $R_2$ is an alkyl, alkenyl, alkynyl, cycloalkyl, cycloalkenyl, bicycloalkyl, optionally substituted phenyl, or heterocycl radical, and $R_3$ is an aromatic heterocyclic, alkyl, alkenyl, alkynyl cycloalkyl, phenyl or naphthyl radical. The novel products of general formula (I), wherein Z is a radical of general formula (II), have remarkable antitumoral activity.

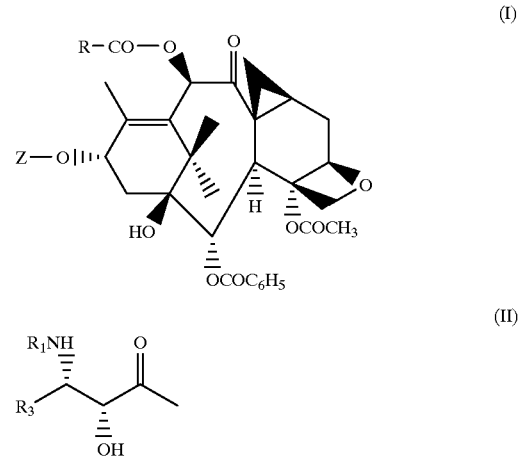

19 Claims, No Drawings

TAXOIDS, PREPARATION THEREOF, AND PHARMACEUTICAL COMPOSITIONS CONTAINING SAME

This application is a 371 of PCT/FR96/00487 dated Apr. 08, 1996.

The present invention relates to new taxoids of general formula:

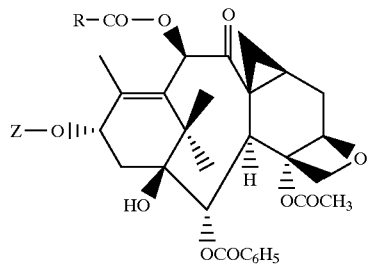

in which:

R represents an unbranched or branched alkyl radical containing 1 to 8 carbon atoms, substituted with a halogen atom chosen from fluorine, chlorine, bromine and iodine atoms or with an amino radical, an alkylamino radical in which the alkyl portion contains 1 to 4 carbon atoms, a dialkylamino radical in which each alkyl portion contains 1 to 4 carbon atoms or, with the nitrogen atom to which it is linked, forms a saturated 5- or 6-membered heterocyclic radical optionally containing a second hetero atom chosen from oxygen, sulphur and nitrogen atoms (and optionally substituted with an alkyl radical containing 1 to 4 carbon atoms or a phenyl radical or a phenylalkyl radical in which the alkyl portion contains 1 to 4 carbon atoms), a carboxyl radical, an alkyloxycarbonyl radical in which the alkyl portion contains 1 to 4 carbon atoms, a cyano or carbamoyl radical, an N-alkylcarbamoyl radical in which the alkyl portion contains 1 to 4 carbon atoms or an N,N-dialkylcarbamoyl radical in which each alkyl portion contains 1 to 4 carbon atoms or, with the nitrogen atom to which it is linked, forms a saturated 5- or 6-membered heterocyclic radical optionally containing a second hetero atom chosen from oxygen, sulphur and nitrogen atoms (and optionally substituted with an alkyl radical containing 1 to 4 carbon atoms or a phenyl radical or a phenylalkyl radical in which the alkyl portion contains 1 to 4 carbon atoms), an alkenyl radical containing 2 to 8 carbon atoms in an unbranched or branched chain, an alkynyl radical containing 2 to 8 carbon atoms in an unbranched or branched chain, a cycloalkyl radical containing 3 to 6 carbon atoms or a cycloalkenyl radical containing 3 to 6 carbon atoms, these radicals being optionally substituted with a halogen atom chosen from fluorine, chlorine, bromine and iodine atoms or with an amino radical, an alkylamino radical in which the alkyl portion contains 1 to 4 carbon atoms, a dialkylamino radical in which each alkyl portion contains 1 to 4 carbon atoms or, with the nitrogen atom to which it is linked, forms a saturated 5- or 6-membered heterocyclic radical optionally containing a second hetero atom chosen from oxygen, sulphur and nitrogen atoms (and optionally substituted with an alkyl radical containing 1 to 4 carbon atoms or a phenyl radical or a phenylalkyl radical in which the alkyl portion contains 1 to 4 carbon atoms), a carboxyl radical, an alkyloxycarbonyl radical in which the alkyl portion contains 1 to 4 carbon atoms, a cyano or carbamoyl radical, an N-alkylcarbamoyl radical in which the alkyl portion contains 1 to 4 carbon atoms or an N,N-dialkylarbamoyl radical in which each alkyl portion contains 1 to 4 carbon atoms or, with the nitrogen atom to which it is linked, forms a saturated 5- or 6-membered heterocyclic radical optionally containing a second hetero atom chosen from oxygen, sulphur and nitrogen atoms (and optionally substituted with an alkyl radical containing 1 to 4 carbon atoms or a phenyl radical or a phenylalkyl radical in which the alkyl portion contains 1 to 4 carbon atoms), or a phenyl radical or a 5- or 6-membered aromatic heterocyclic radical containing an oxygen, sulphur or nitrogen atom as hetero atom, and Z represents a hydrogen atom or a radical of general formula:

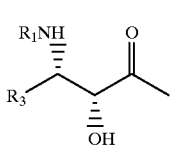

in which:

$R_1$ represents a benzoyl radical optionally substituted with one or more identical or different atoms or radicals chosen from halogen atoms and alkyl radicals containing 1 to 4 carbon atoms, alkoxy radicals containing 1 to 4 carbon atoms or trifuloromethyl radicals, a thenoyl or furoyl radical or a radical $R_2$—O—CO— in which $R_2$ represents:

an alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms or a cycloalkenyl radical containing 4 to 6 carbon atoms or a bicycloalkyl radical containing 7 to 10 carbon atoms, these radicals being optionally substitute with one or more substitutents chosen from halogen atoms and hydroxyl radicals, alkoxy radicals containing 1 to 4 carbon atoms, dialkylamino radicals in which each alkyl portion contains 1 to 4 carbon atoms, piperidino or morpholino radicals, 1-piperazinyl radicals (optionally substituted at position 4 with an alkyl radical containing 1 to 4 carbon atoms or with a phenylalkyl radical in which the alkyl portion contains 1 to 4 carbon atoms), cycloalkyl radicals containing 3 to 6 carbon atoms, cycloalkenyl radicals containing 4 to 6 carbon atoms, phenyl radicals (optionally substituted with one or more atoms or radicals chosen from halogen atoms and alkyl radicals containing 1 to 4 carbon atoms or alkoxy radicals containing 1 to 4 carbon atoms), cyano or carboxyl radicals or alkoxycarbonyl radicals in which the alkyl portion contains 1 to 4 carbon atoms, a phenyl or α- or β-naphthyl radical optionally substituted with one or more atoms or radicals chosen from halogen atoms and alkyl radicals containing 1 to 4 carbon atoms or alkoxy radicals containing 1 to 4 carbon atoms, or a 5-membered aromatic heterocyclic radical preferably chosen from furyl and thienyl radicals, or a saturated heterocyclic radical containing 4 to 6 carbon atoms, optionally substituted with one or more alkyl radicals containing 1 to 4 carbon atoms, $R_3$ represents an unbranched or branched alkyl radical containing 1 to 8 carbon atoms, an unbranched or branched alkenyl radical containing 2 to 8 carbon atoms, an unbranched or branched alkynyl radical containing 2 to 8 carbon atoms, a cycloalkyl radical containing 3 to 6 carbon atoms, a phenyl or α- or β-naphthyl radical optionally substituted with one or more atoms or radicals chosen from halogen atoms and alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, or a 5- or 6-membered aromatic heterocycle containing one or more identical or different hetero atoms chosen from nitrogen, oxygen and sulphur atoms and optionally substituted with one or more identical or different substituents chosen from halogen atoms and alkyl, alkoxy, aryl, aryloxy, amino, alkylamino, dialkylamino, acylamino, alkoxycarbonylamino, acyl, arylcarbonyl, cyano, carboxyl, carbamoyl, alkylcarbamoyl, dialkylcarbamoyl or alkyloxycarbonyl radicals, on the understanding that, in the substitutents of the phenyl, α- or β-naphthyl and aromatic heterocyclic radicals, the alkyl radicals and the alkyl portions of the other radicals contain 1 to 4 carbon atoms, and that the alkenyl and alkynyl radicals contain 2 to 8 carbon atoms, and that the aryl radicals are phenyl or α- or β-naphthyl radicals.

Among the compounds described in the prior art, there may be mentioned Patent FR 2,698,871, which describes compunds bearing a cyclopropyl group at position 7–8 and bearing at position 10 either a hydroxyl group or an acetyl group, the other substituents being similar to those of the present invention.

U.S. Pat. No. 5,254,580 describes compounds bearing a cyclopropyl group at position 7–8 and bearing at position 10 a group —OCOR, —OCOOR, H, OH, or CO. These derivatives are all different from the derivatives of the present invention.

Preferably, the aryl radicals which can be represented by $R_3$ are phenyl or α- or β-naphthyl radicals optionally substituted with one or more atoms or radicals chosen from halogen atoms (fluorine, chlorine, bromine, iodine) and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, on the understanding that the alkyl radicals and the alkyl portions of the other radicals contain 1 to 4 carbon atoms, that the alkenyl and alkynyl radicals contain 2 to 8 carbon atoms and that the aryl radicals are phenyl or α- or β-naphthyl radicals.

Preferably, the heterocyclic radicals which can be represented by $R_3$ are 5- or 6-membered aromatic heterocyclic radicals containing one or more identical or different atoms chosen from nitrogen, oxygen and sulphur atoms, optionally substituted with one or more identical or different substitutents chosen from halogen atoms (fluorine, chlorine, bromine, iodine) and alkyl radicals containing 1 to 4 carbon atoms, aryl radicals containing 6 to 10 carbon atoms, alkoxy radicals containing 1 to 4 carbon atoms, aryloxy radicals containing 6 to 10 carbon atoms, amino radicals, alkylamino radicals containing 1 to 4 carbon atoms, dialkylamino radicals in which each alkyl portion contains 1 to 4 carbon atoms, acylamino radicals in which the acyl portion contains 1 to 4 carbon atoms, alkoxycarbonylamino radicals containing 1 to 4 carbon atoms, acyl radicals containing 1 to 4 carbon atoms, arylcarbonyl radicals in which the aryl portion contains 6 to 10 carbon atoms, cyano, carboxyl or carbomyl radicals, alkylcarbamoyl radicals in which the alkyl portion contains 1 to 4 carbon atoms, dialkylcarbamoyl radicals in which each alkyl portion contains 1 to 4 carbon atoms or alkoxycarbonyl radicals in which the alkoxy portion contains 1 to 4 carbon atoms.

Preferably, R represents an alkyl radical containing 1 to 8 carbon atoms, substituted with a halogen atom or with a dimethylamino or diethylamino, carboxyl, methoxycarbonyl, ethoxycarbonyl, cyano, carbamoyl, N-methylcarbomoyl, N,N-dimethylcarbamoyl, pyrrolidinocarbonyl or piperidinocarbonyl radical, an alkenyl radical containing 2 to 8 carbon atoms, an alkynyl radical containing 2 to 8 carbon atoms, a cycloalkyl radical containing 3 to 6 carbon atoms or a cycloalkenyl radical containing 3 to 6 carbon atoms, optionally substituted with a halogen atom or with a dimethylamino, diethylamino, carboxyl, methoxycarbonyl, ethoxycarbonyl, cyano, carbamoyl, N-methylcarbamoyl, N,N-dimethylcarbamoyl, pyrrolidinocarbonyl or piperidinocarbonyl radical, or a phenyl, 2-pyridyl, 3-pyridyl, 4-pyridyl, 2-thienyl, 3-thienyl, 2-furyl, 3-furyl or 2-, 4- or 5-thiazolyl radical.

More especially, the invention relates to the products of general formula (I) in which Z represents a hydrogen atom or a radical of general formula (II) in which $R_1$ represents a benzoyl radical or a radical $R_2$-13 O—CO— in which $R_2$ represents a tert-butyl radical and $R_3$ represents an alkyl radical containing 1 to 6 carbon atoms, an alkenyl radical containing 2 to 6 carbon atoms, a cycloalkyl radical containing 3 to 6 carbon atoms, a phenyl radical optionally substituted with one or more identical or different atoms or radicals chosen from halogen atoms (fluorine, chlorine) and alkyl (methyl), alkoxy (methoxy), dialkylamino (dimethylamino), acylamino (acetylamino), alkoxycarbonylamino (tert-butoxycaronylamino) or trifluoromethyl radicals, or a 2- or 3-furyl, 2- or 3-thienyl or 2, 4- or 5-thiazolyl radical, and R represents a cycloalkyl radical containing 3 to 6 carbon atoms or a phenyl, 2-, 3- or 4-pyridyl, 2- or 3-furyl and 2- or 3-thienyl radical.

Still more especially, the invention relates to the products of general formula (I) in which Z represents a hydrogen atom or a radical of general formula (II) in which $R_1$ represents a benzoyl radical or a radical $R_2$—O—CO— in which $R_2$ represents a tert-butyl radical and $R_3$ represents an isobutyl, isobutenyl, butenyl, cyclohexyl, phenyl, 2-furyl, 3-furyl, 2-thienyl, 3-thienyl, 2-thiazolyl, 4-thiazolyl or 5-thiazolyl radical, and R represents a cyclopropyl, cyclopentyl, phenyl, 2-pyridyl, 2-thienyl or 2-furyl radical.

The products of general formula (I) in which Z represents a radical of general formula (II) display noteworthy antitumour and antileukaemic properties.

According to the invention, the products of general formula (I) in which Z represents a radical of general formula (II) may be obtained by esterification of a product of general formula:

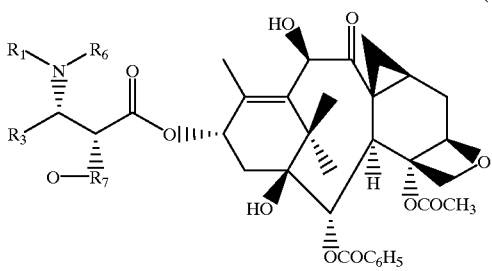

(III)

in which $R_1$ and $R_3$ are defined as above, and either $R_6$ represents a hydrogen atom and $R_7$ represents a group protecting the hydroxyl function, or $R_6$ and $R_7$ together form a saturated 5- or 6-membered heterocycle, by means of an acid of general formula:

$$R\text{—}CO\text{—}OH \qquad (IV)$$

in which R is defined as above, or by means of a derivative of this acid, such as a halide, the symmetrical anhydride or a mixed anhydride, to obtain a product of general formula:

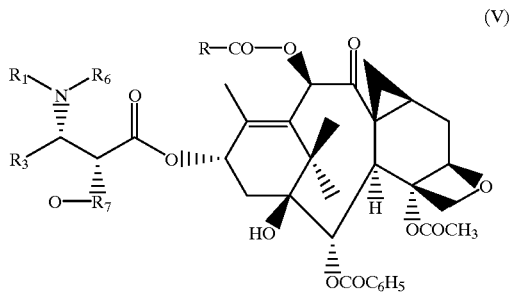

(V)

in which $R_1$, $R_3$, $R_6$ and $R_7$ are defined as above, followed by replacement of the protective groups $R_7$ or $R_6$ and $R_7$ by hydrogen atoms.

The esterification by means of an acid of general formula (IV) may be performed in the presence of a condensing agent (carbodiimide, reactive carbonate) and an activating agent (aminopyridines) in an organic solvent (ether, ester, ketones, nitriles, aliphatic hydrocarbons, halogenated aliphatic hydrocarbons, aromatic hydrocarbons) at a temperature of between −10 and 90° C.

The esterification may also be carried out using the acid of general formula (IV) in the form of the symmetrical anhydride, working in the presence of an activating agent (aminopyridines) in an organic solvent (ethers, esters, ketones, nitriles, aliphatic hydrocarbons, halogenated aliphatic hydrocarbons, aromatic hydrocarbons) at a temperature of between 0 and 90° C.

The esterification may also be carried out using the acid of general formula (IV) in halide form or in the form of a mixed anhydride with an aliphatic or aromatic acid, optionally prepared in situ, in the presence of a base (tertiary aliphatic amine), working in an organic solvent (ethers, esters, ketones, nitriles, aliphatic hydrocarbons, halogenated aliphatic hydrocarbons, aromatic hydrocarbons) at a temperature of between 0 and 80° C.

When $R_6$ represents a hydrogen atom, $R_7$ preferably represents a methoxymethyl, 1-ethoxyethyl, benzyloxymethyl, trimethylsilyl, triethylsilyl, β-trimethylsilylethoxymethyl, benzyloxycarbonyl or tetrahydropyranyl radical.

When $R_6$ and $R_7$ together form a heterocycle, the latter is preferably an oxazolidine ring optionally monosubstituted or gem-disubstituted at position 2.

Replacement of the protective groups $R_7$ and/or $R_6$ and $R_7$ by hydrogen atoms may be performed, depending on their nature, in the following manner:

1) when $R_6$ represents a hydrogen atom and $R_7$ represents a group protecting the hydroxyl function, replacement of the protective groups by hydrogen atoms is performed by means of an inorganic acid (hydrochloric acid, sulfuric acid, hydrofluoric acid) or organic acid (acetic acid, methanesulphonic acid, trifluoromethanesulphonic acid, p-tolunesulphonic acid) used alone or mixed, working in an organic solvent chosen from alcohols, ethers, esters, aliphatic hydrocarbons, halogenated aliphatic hydrocarbons, aromatic hydrocarbons or nitriles at a temperature of between −10 and 60° C., 2) when $R_6$ and $R_7$ together form a saturated 5- or 6-membered heterocycle, and more especially an oxazolidine ring of general formula:

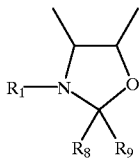

(VI)

in which $R_1$ is defined as above and $R_8$ and $R_9$, which may be identical or different, represent a hydrogen atom or an alkyl radical containing 1 to 4 carbon atoms, or an aralkyl radical in which the alkyl portion radical contains 1 to 4 carbon atoms and the aryl portion preferably represents a phenyl radical optionally substituted with one or more alkoxy radicals containing 1 to 4 carbon atoms, or an aryl radical preferably representing a phenyl radical optionally substituted with one or more alkoxy radicals containing 1 to 4 carbon atoms, or alternatively $R_8$ represents an alkoxy radical containing 1 to 4 carbon atoms or a trihalomethyl radical such as trichloromethyl or a phenyl radical substituted with a trihalomethyl radical such as trichloromethyl and $R_9$ represents a hydrogen atom, or alteratively $R_8$ and $R_9$, together with the carbon atom to which they are linked, form a 4- to 7- membered ring, replacement of the protective group formed by $R_6$ and $R_7$ by hydrogen atoms may be performed, depending on the meanings of $R_1$, $R_8$ and $R_9$, in the following manner:

a) when $R_1$ represents a tert-butoxycarbonyl radical and $R_8$ and $R_9$, which may be identical or different, represent a hydrogen atom or an alkyl radical or an aralkyl (benzyl) or aryl (phenyl) radical, or alternatively $R_8$ represents a trihalomethyl radical or a phenyl radical substituted with a trihalomethyl radical and $R_9$ represents a hydrogen atom, or alternatively $R_8$ and $R_9$ together form a 4- to 7-membered ring, treatment of the ester of general formula (V) with an inorganic or organic acid, where appropriate in an organic solvent such as an alcohol, yields the product of general formula:

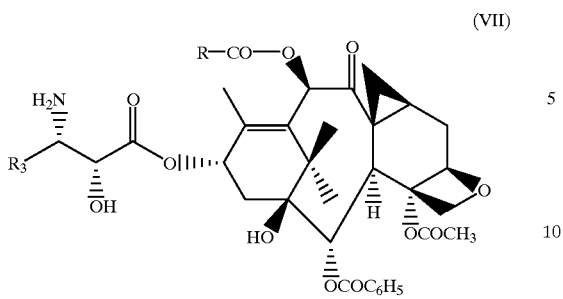

(VII)

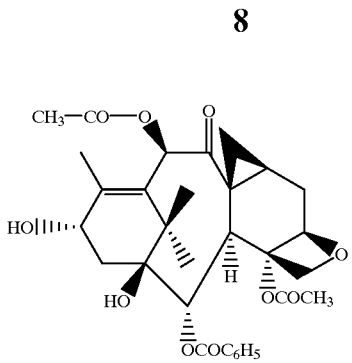

(IX)

in which $R_3$ is defined as above, which is acylated by means of benzoyl chloride in which the phenyl ring is optionally substituted or by means of thenoyl chloride, of furoyl chloride or of a product of general formula:

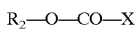

$R_2$—O—CO—X  (VIII)

in which $R_2$ is defined as above and X represents a halogen atom (fluorine, chlorine) or a residue —O—$R_2$ or —O—CO—O—$R_2$, to obtain product of general formula (I) in which Z represents a radical of general formula (II).

Preferably the product of general formula (V) is treated with formic acid at a temperature in the region of 20° C. to yield the product of general formula (VII).

Preferably, the acylation of the product of general formula (VII) by means of a benzoyl chloride in which the phenyl radical is optionally substituted or by means of thenoyl chloride, of furoyl chloride or of a product of general formula (VIII) is performed in an inert organic solvent chosen from esters such as ethyl acetate, isopropyl acetate or n-butyl acetate and halogenated aliphatic hydrocarbons such as dichloromethane or 1,2-dichloroethane, in the presence of an inorganic base such as sodium bicarbonate or an organic base such as trimethylamine. The reaction is performed at a temperature of between 0 and 50° C., and preferably in the region of 20° C.

b) when $R_1$ represents an optionally substituted benzoyl radical, a thenoyl or furoyl radical or a radical $R_2O$—CO— in which $R_2$ is defined as above, $R_8$ represents a hydrogen atom or an alkoxy radical containing 1 to 4 carbon atoms or a phenyl radical substituted with one or more alkoxy radicals containing 1 to 4 carbon atoms and $R_9$ represents a hydrogen atom, replacement of the protective group formed by $R_6$ and $R_7$ by hydrogen atoms is performed in the presence of an inorganic acid (hydrochloric acid, sulfuric acid) or organic acid (acetic acid, methanesulphonic acid, trifuloromethanesulphonic acid, p-toluenesulphonic acid) used alone or mixed in a stoichiometric or catalytic amount, working in an organic solvent chosen from alcohols, ethers, esters, aliphatic hydrocarbons, halogenated aliphatic hydrocarbons and aromatic hydrocarbons at a temperature of between –10 and 60° C., and preferably between 15 and 30° C.

The products of general formula (III) may be obtained under the conditions described in U.S. Pat. No. 5,532,388.

The products of general formula (III) may also be obtained by esterification of a baccatin III derivative of formula:

by means of an acid of general formula:

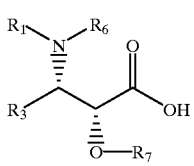

(X)

in which $R_1$, $R_3$, $R_6$ and $R_7$ are defined as above, or by means of a derivative of this acid such as a halide, the symmetrical anhydride or a mixed anhydride, and then replace the acetoxy radical at position 10 by a hydroxyl radical.

The esterification is performed under conditions similar to those described above for the esterification of a product of general formula (III) by means of an acid of general formula (IV).

Replacement of the acetoxy radical at position 10 by a hydroxyl radical is generally performed by means of zinc iodide.

The product of formula (IX) may be obtained under the conditions described in International Application PCT WO 94/13654, by the action of an alkali metal halide (sodium iodide, potassium fluoride) or an alkali metal azide (sodium azide) or a quaternary ammonium salt or an alkali metal phosphate on 2α-benzoyloxy-4α,10β-diacetoxy-1β,13α-dihydroxy-5β,20-epoxy-7β-trifluoromethylsulphonyloxy-9-oxo-11-taxene.

The products of general formula (I) in which Z represents a radical of general formula (II) may also be obtained by esterification of a product of general formula:

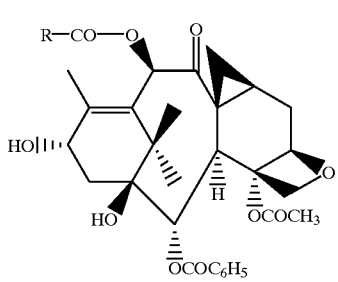

(XI)

in which R is defined as above, by means of an acid of general formula (X) or of a derivative of this acid such as a halide, the symmetrical anhydride or a mixed anhydride, to obtain a product of general formula (V) in which the protective groups $R_7$ or $R_6$ and $R_7$ are replaced by hydrogen atoms under the conditions described above.

The products of general formula (XI), that is to say the products of general formula (I) in which Z represents a hydrogen atom, may be obtained by esterification of a product of formula:

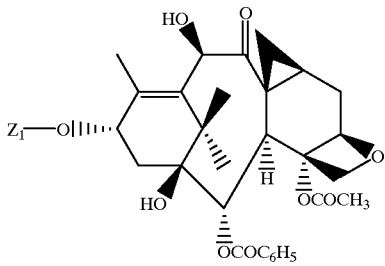

(XII)

in which $Z_1$ represents a group protecting the hydroxyl function, such as a silyl radical, for instance a triethylsilyl radical, by means of an acid of general formula (IV) or of a derivative of this acid such as a halide or the symmetrical anhydride or a mixed anhydride, under the conditions described above for the esterification of a product of general formula (III) by means of an acid of general formula (IV) or of a derivative of this acid, followed by replacement of the protective group $Z_1$ by a hydrogen atom under conditions which do not affect the remainder of the molecule.

The product of general formula (XII) may be obtained under the conditions described in U.S. Pat. No. 5,532,388.

The new products of general formula (I) obtained by carrying out the processes according to the invention may be purified according to known methods such as crystallization or chromatography.

The products of general formula (I) in which Z represents a radical of general formula (II) display noteworthy biological properties.

In vitro, measurement of the biological activity is performed on tubulin extracted from pig's brain by the method of M. L. Shelanski, et al., Proc. Natl. Acad. Sci. USA, 70, 765–768 (1973). Study of the depolymerization of microtubules to tubulin is performed according to the method of G. Chauvière et al., C. R. Acad. Sci., 293, series II, 501–503 (1981). In this study, the products of general formula (I) in which Z represents a radical of general formula (II) were shown to be at least as active as taxol and Taxotere.

In vivo, the products of general formula (I) in which Z represents a radical of general formula (II) were shown to be active in mice grafted with B16 melanoma at doses of between 1 and 10 mg/kg administered intraperitioneally, as well as on other liquid or solid tumours.

The new products have antitumour properties, and more especially activity against tumours which are resistant to Taxol® or to Taxotere®. Such tumours comprise colon tumours which have a high expression of the mdr 1 gene (multiple drug resistance gene). Multiple drug resistance is a customary term relating to the resistance of a tumour to different products having different structures and mechanisms of action. Taxoids are generally known to be strongly recognized by experimental tumours such as P388/DOX, a cell line selected for its resistance to doxorubicin (DOX) which overexpresses mdr 1.

The examples which follow illustrate the present invention.

EXAMPLE 1

380 mg of 4α-acetoxy-2α-benzoyloxy-1β,10β-dihydroxy-5β20-epoxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidone-5-carboxylate, 25 mg of 4-(dimethylamino)pyridine, 0.5 g of 4 Å molecular sieve and 151 mg of N,N'-dicyclohexylcarbodiimide are added at a temperature in the region of 20° C. to a solution, maintained under an argon atmosphere and kept stirring, of 62 mg of 2-pyridine-carboxylic acid in 25 cm³ of anhydrous ethyl acetate. The reaction mixture is kept stirring for 16 hours at a temperature in the region of 20° C., and 20 mg of 2-pyridinecarboxylic acid, 8 mg of 4-(dimethylamino)-pyridine, 100 mg of 4 Å molecular sieve and 50 mg of N,N'-dicyclohexylcarbodiimide are then added and the mixture is kept stirring again for 4 hours. The reaction mixture is filtered through sintered glass lined with Celite. The sintered glass is washed with 100 cm³ of ethyl acetate, and the filtrates are combined, washed successively with 15 cm³ of saturated aqueous sodium hydrogen carbonate solution and with 5 times 10 cm³ of distilled water, dried over magnesium sulphate, filtered and concentrated to dryness under reduced pressure (2.7 kPa) at 40° C. 715 mg of a white foam are obtained, which product is purified by chromatography on 40 g of silica (0.04–0.063 mm) contained in a column 2 cm in diameter [eluent: dichloromethane/methanol (99:1 by volume)], collecting 10-cm³ fractions. Fractions containing only the desired product are pooled and concentrated to dryness under reduced pressure (2.7 kPa) at 40° C. 297 mg of 4α-acetoxy-2α-benzoyloxy-5β,20-epoxy-1β-hydroxy-7β,8β-methylene-9-oxo-10β-(2-pyridylcarbonyl)oxy-19-nor-11-taxen-13α-yl (2R,4S,5R)-3-tert-butoxycarbonyl-2-(4-methoxyphenyl)-4-phenyl-1,3-oxazolidine-5-carboxylate are thereby obtained in the form of a white foam.

290 mg of 4α-acetoxy-2α-benzoyloxy-5β,20-epoxy-1β-hydroxy-7β,8β-methylene-9-oxo-10β-(2-pyridylcarbonyl)oxy-19-nor-11-taxen-13α-yl (2R,4S,5R)-3-tert-butoxycarbonyl-2-(4-methoxyphenyl)-4-phenyl-1,3-oxazolidine-5-carboxylate are dissolved in 5.7 cm³ of 0.1N ethanolic hydrochloric acid solution. The solution thereby obtained is stirred for 1 hour at a temperature in the region of 20° C. and then concentrated to dryness under reduced pressure (2.7 kPa) at a temperature in the region of 40° C. The residual solid is dissolved in 50 cm³ of dichloromethane, and the solution obtained is washed successively two times with 3 cm³ of saturated aqueous sodium hydrogen carbonate solution and with 3 times 5 cm³ of distilled water, dried over magnesium sulphate, filtered and concentrated to dryness under reduced pressure (2.7 kPa) at 40° C. 270 mg of a white foam are obtained, which product is purified by chromatography on 30 g of silica (0.04–0.63 mm) contained in a column 2 cm in diameter [eluent: dichloromethane/methanol (99:1 by volume)], collecting 10-cm³ fractions. Fractions containing only the desired product are pooled and concentrated to dryness under reduced pressure (0.27 kPa) at 20° C. for 16 hours. 189 mg of 4α-acetoxy-2α-benzoyloxy-5β,20-epoxy-1β-hydroxy-7β,8β-methylene-9-oxo-10β-(2-pyridylcarbonyl)oxy-19-nor-11-taxen-13α-yl (2R,3S)-3-tert-butoxycarbonylamino-2-hydroxy-3-phenylpropionate are thereby obtained in the form of a white foam, the characteristics of which are as follows:

optical rotation: $[\alpha]_D^{20}$=−24 (c=0.52; methanol)

¹H NMR spectrum (300 MHz; CDCl₃; chemical shifts δ in ppm; coupling constant J in Hz): 1.28 (s, 9H: —C(CH₃)₃); 1.41 (s, 3H: —CH₃ at position 16 or 17); 1.44 (mt, 1H: —H at position 7); 1.57 (s, 3H: —CH₃ at position 16 or 17); 1.69 and 2.25 (respectively dd and mt, J=6 and 5.5, 1H each: —CH₂— at position 19);

1.89 (s, 1H: —O$\underline{H}$ at position 1); 1.92 (s, 3H: —C$\underline{H}_3$); 2.11 and 2.50 (respectively broad d and dt, J=16 and J=16 and 4.5 Hz, 1H each: —C$\underline{H}_2$ at position 6); 2.25 and 2.39 (2 mt, 1H each: —C$\underline{H}_2$ at position 14); 2.40 (s, 3H: —COC$\underline{H}_3$); 3.29 (mt, 1H: —O$\underline{H}$ at position 2'); 4.04 and 4.32 (2 d, J=9, 1H each: —C$\underline{H}_2$ at position 20); 4.15 (d, J=7.5, 1H: —$\underline{H}$ at position 3); 4.62 (mt, 1H: —$\underline{H}$ at position 2'); 4.74 (d, J=4.5, 1H: —H at position 5); 5.28 (broad d, J=10, 1H: —$\underline{H}$ at position 3'); 5.35 (d, J=10, 1H: —CON$\underline{H}$—); 5.61 (d, J=7.5, 1H: —$\underline{H}$ at position 2); 6.28 (broad t, J=9, 1H: —$\underline{H}$ at position 13); 6.64 (s, 1H: —$\underline{H}$ at position 10); from 7.25 to 7.45 (mt, 5H: —C$_6$$\underline{H}_5$ at position 3'); 7.51 [(mt, 3H: —OCOC$_6$H$_5$ (—$\underline{H}$ at position 3 and $\underline{H}$ at position 5) and —C$_5$H$_4$N (—$\underline{H}$ at position 5)]; 7.60 [(t, J=7.5 1H: —OCOC$_6$H$_5$ (—$\underline{H}$ at position 4)]; 7.85 [(dt, J=8 and 1.5, 1H: —C$_5$H$_4$N (—$\underline{H}$ at position 4)]; 8.11 [(d, J=8, 1H: —C$_5$H$_4$N (—$\underline{H}$ at position 3)]; 8.15 [(d, J=7.5, 2H: —OCOC$_6$H$_5$ (—$\underline{H}$ at position 2 and —H at position 6)]; 8.80 [(broad d, J=4.5, 1H: —C$_5$H$_4$N (—H at position 6)].

4α-acetoxy-2α-benzoyloxy-1β,10β-dihydroxy-5β,20-epoxy-1β-hydroxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate may be prepared in the following manner:

20 g of powdered 4 Å molecular sieve and 9.3 g of zinc iodide are added at a temperature in the region of 20° C. to a solution, maintained under an argon atmosphere and kept stirring, of 5.5 g of 2α-benzoyloxy-4α,10β-diacetoxy-5β,20-epoxy-1β-hydroxy-7β,8β-methylene-9-oxo-19-nor-11-taxen-13α-yl (2R,4S,5R)-3-tert-butoxycarbonyl-2-(4-methoxyphenyl)-4-phenyl- 1,3-oxazolidine-5-carboxylate in 200 cm$^2$ of anhydrous methanol. The reaction mixture is kept stirring for 3 hours at a temperature in the region of 20° C., a further 3.72 g of zinc iodide and 4 g of 4 Å molecular sieve are then added and stirring is continued for 24 hours at a temperature in the region of 20° C. The reaction mixture is filtered through sintered glass lined with Celite. The sintered glass is washed with 100 cm$^3$ of dichloromethane, and the filtrates are combined and poured into 200 cm$^3$ of distilled water. The two-phase mixture is stirred for 30 minutes, and the aqueous phase is then separated after settling has taken place and re-extracted with 3 times 200 cm$^3$ of dichloromethane. The organic phases are combined, washed with 50 cm$^3$ of distilled water, dried over magnesium sulphate, filtered and concentrated to dryness under reduced pressure (2.7 kPa) at 40° C. 5.3 g of a white foam are obtained, which product is purified by chromatography on 160 g of silica (0.04–0.063 mm) contained in a column 3.8 cm in diameter [eluent: dichloromethane/methanol (99:1 by volume)], collecting 100-cm$^3$ fractions. Fractions containing only the desired product are pooled and concentrated to dryness under reduced pressure (2.7 kPa) at 40° C. 3.7 g of a white foam are thereby obtained, which product is reputrified by chromatography on 175 g of silica (0.04–0.063 mm) contained in a column 3.8 cm in diameter [eluent: dichloromethane/methanol (99.6:0.4 by volume)], collecting 50-cm$^3$ fractions. Fractions containing only the desired product are pooled and concentrated to dryness under reduced pressure (2.7 kPa) at 40° C. 1.78 g of 4α-acetoxy-2-benzoyloxy-1β,10β-dihydroxy-5β,20-epoxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate are thereby obtained in the form of a white form.

2α-Benzoyloxy-4α,10β-diacetoxy-5β,20-epoxy-1β-hydroxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate may be prepared in the following manner:

4.75 g of 2α-benzoyloxy-4α,10β-diacetoxy-1β,13α-dihydroxy-5β,20-epoxy-7β,8β-methylene-9-oxo-19-nor-11-taxene, 0.5 g of 4-(dimethylamino)pyridine and 3.01 g of N,N'-dicyclohexylcarbodiimide are added at a temperature in the region of 20° C. to a solution, maintained under an argon atmosphere and kept stirring, of 4.01 g of (2R,4S,5R)-3-tert-butoxycarbonyl-2-(4-methoxyphenyl)-4-phenyl-1,3-oxazolidine-5-carboxylic acid in 190 cm$^3$ of anhydrous ethyl acetate. The reaction mixture is kept stirring for 2 hours at a temperature in the region of 20° C. and then filtered through sintered glass lined with Celite. The sintered glass is washed two times with 50 cm$^3$ of ethyl acetate, and the filtrates are combined, washed with 5 times 50 cm$^3$ of distilled water, dried over magnesium sulphate, filtered and concentrated to dryness under reduced pressure (2.7 kPa) at 40° C. 9.67 g of a yellow foam are obtained, which product is taken up with 70 cm$^3$ of diisopropyl ether. The suspension obtained is stirred for 1 hour at a temperature in the region of 20° C. and then filtered through sintered glass. The sintered glass is washed with twice 20 cm$^3$ of diisopropyl ether, and the filtrates are combined and concentrated to dryness under reduced pressure (2.7 kPa) at 40° C. 8.09 g of a yellow foam are obtained, which product is purified by chromatography of 250 g of silica (0.063–0.2 mm) contained in a column 3.8 cm in diameter [eluent: dichloromethane/methanol (99:1 by volume)], collecting 100-cm$^3$ fractions. Fractions containing only the desired product are pooled and concentrated to dryness under reduced pressure (2.7 kPa) at 40° C. 7.23 g of 2α-benzoyloxy-4α,10β-diacetoxy-5β,20-epoxy-1β-hydroxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate are thereby obtained in the form of a white foam.

(2R,4S,5R)-3-tert-Butoxycarbonyl-2-(4-methoxyphenyl)-4-phenyl-1,3-oxazolidine-5-carboxylic acid may be prepared in the following manner:

A solution of 10.0 g of methyl (2R,3S)-3-t-butoxycarbonylamino-2-hydroxy-3-phenylpropionate and 0.25 g of pyridium p-toluenesulphonate in 200 cm$^3$ of toluene is dehydrated by distilling off 20 cm$^3$ of solvent. 6.34 cm$^3$ of p-methoxybenzaldehyde dimethyl acetal are added over 5 minutes to the reaction mixture heated to boiling. During the addition, 50 cm$^3$ of solvent are distilled off, and a further 100 cm$^3$ of solvent are then distilled off. After cooling to a temperature in the region of 20° C., 80 cm$^3$ of cyclohexane are added over 10 minutes. The mixture is cooled to 0–5° C. The slurry obtained is filtered through sintered glass, and the filter cake is washed with 40 cm$^3$ of cyclohexane and then dried under reduced pressure at a temperature in the region of 20° C. 10.39 g of (2R,4S,5R)-3-t-butoxycarbonyl-2-(4-methoxyphenyl)-4-phenyl-5-methoxycarbonyl-1,3-oxazolidine are thereby obtained in a 74% yield, the characteristics of which product are as follows:

infrared spectrum (in disk with KBr): characteristic absorption bands at 3100–3000, 2980, 2960, 2930, 2910, 2840, 1740, 1700, 1614, 1514, 1460, 1435, 1390, 1370, 1245, 1175, 1165, 816, 760 and 700 cm$^{-1}$ proton nuclear magnetic resonance spectrum (400 MHz; CDCl$_3$; temperature: 323° K; chemical shifts δ in ppm; coupling constants J in Hz): 1.11 (s, 9H); 3.60 (s, 3H); 3.82 (s, 3H); 4.58 (d, J=5, 1H); 5.42 (broad d, J=5,1H); 6.38 (broad s, 1H); 6.92 (d, J=7.5, 2H); 7.30 to 7.45 (mt, 7H).

14 cm³ of an aqueous solution containing 0.31 g of lithium hydroxide monohydrate are added to a solution of 3.0 g of the product obtained above in 27 cm³ of methanol. The mixture is stirred for 2 hours at a temperature in the region of 20° C. The methanol is removed by distillation under reduced pressure and 40 cm³ of dichloromethane are then added. With vigorous stirring, the reaction mixture is acidified by adding 1N hydrochloric acid to pH 1. After settling has taken place, the aqueous phase is separated and extracted twice with 40 cm³ of dichloromethane. The combined organic phases are dried over sodium sulphate. After filtration and evaporation of the solvent, 2.88 g of (2R,4S,5R)-3-t-butoxycarbonyl-2-(4-phenyl-1,3-oxazolidine-5-carboxylic acid are obtained in a 94.5% yield, the characteristics of which product are as follows:

infrared spectrum (in disk with KBr): characteristic absorption bands at 3325–2675, 2980, 2955, 2935, 2845, 1755, 1700, 1615, 1590, 1515, 1460, 1250, 1175, 1030, 835, 765 and 705 cm$^{-1}$ proton nuclear magnetic resonance spectrum (250 MHz; CDCl$_3$; chemical shifts δ in ppm; coupling constants J in Hz): 1.08 (s, 9H); 3.82 (s, 3H); 4.61 (d, J=5, 1H); 5.42 (broad d, J=5, 1H); 6.38 (broad s, 1H); 6.92 (d, J=7.5, 2H); 7.30 to 7.45 (mt, 7H).

2α-Benzoyloxy-4α,10β-diacetoxy-1β,13α-dihydroxy-5β,20-epoxy-7β,8β-methylene-9-oxo-19-nor-11-taxene may be prepared in the following manner:

1.9 g of powdered 4 Å molecular sieve and 5.8 g of sodium chloride are added at a temperature in the region of 20° C. to a solution, maintained under an argon atmosphere and kept stirring, of 3.85 g of 2α-benzoyloxy-4α,10β-diacetoxy-1β,13α-dihydroxy-5β,20-epoxy-9-oxo-7β-trifluoromethylsulphonyloxy-11-taxene in a mixture of 75 cm³ of acetonitrile and 7.5 cm³ of anhydrous tetrahydrofuran. The reaction mixture is stirred for 30 minutes at a temperature in the region of 20° C., then heated to reflux (75° C.) and kept refluxing for 2.5 hours. After cooling to a temperature in the region of 20° C., the reaction mixture is filtered through sintered glass. The sintered glass is washed with 3 times 80 cm³ of dichloromethane, and the filtrates are combined, washed successively with 25 cm³ of saturation aqueous sodium hydrogen carbonate solution and two times with 25 cm³ of distilled water, dried over magnesium sulphate, filtered and concentrated to dryness under reduced pressure (2.7 kPa) at 40° C. 3.5 g of a white foam are obtained, which product is purified by chromatography of 140 g of silica (0.063–0.2 mm) contained in a column 3.5 cm in diameter [eluent: dichloromethane/methanol (99:1 by volume)], collecting 50-cm³ fractions. Fractions containing only the desired product are pooled and concentrated to dryness under reduced pressure (2.7 kPa) at 40° C. 2.7 g of 2α-benzoyloxy-4α,10β-diacetoxy-1β,13α-dihydroxy-5β,20-epoxy-7β,8β-methylene-9-oxo-19-nor-11-taxene are thereby obtained in the form of a white foam.

2α-Benzoyloxy-4α,10β-diacetoxy-1β,13α-dihydroxy-5β,20-epoxy-9-oxo-7β-trifluoromethylsulphonyloxy-11-taxene may be prepared in the following manner:

0.32 cm³ of anhydrous pyridine are added at a temperature in the region of 20° C. to a solution, maintained under an argon atmosphere and kept stirring, of 0.59 g of 2α-benzoyloxy-4α,10β-diacetoxy-5β,20-epoxy-9-oxo-1β,7β,13α-trihydroxy-11-taxene (baccatin III) in 50 cm³ of dichloromethane, and 0.25 cm³ of trifluoromethanesulphonic anhydride are then added dropwise at a temperature in the region of 20° C. The reaction medium is then heated to reflux (40° C.) for 3 hours, a further 0.08 cm³ of trifluoromethanesulphonic anhydride is added thereafter and heating to reflux is continued for 1 hour. After cooling to a temperature in the region of 20° C., the reaction medium is poured into a mixture of 50 cm³ of dichloromethane and 20 cm³ of distilled water. The organic phase is separated after settling has taken place, washed successively with 10 cm³ of 1N aqueous hydrochloric acid solution and with twice 10 cm³ of distilled water, dried over magnesium sulphate, filtered and concentrated to dryness under reduced pressure (2.7 kPa) at 40° C. 0.75 g of a white foam is obtained, which product is purified by chromatography on 60 g of silica (0.063–0.2 mm) contained in a column 2.5 cm in diameter [eluent: dichloromethane/methanol (98.5:1.5 by volume)], collecting 20-cm³ fractions. Fractions containing only the desired product are pooled are concentrated to dryness under reduced pressure (2.7 kPa) at 40° C. 0.675 g of 2α-benzoyloxy-4α,10β-diacetoxy-1β,13α-dihydroxy-5β,20-epoxy-9-oxo-7β-trifluoromethylsulphonyloxy-11-taxene is thereby obtained in the form of a white foam.

2α-Benzoyloxy-4α,10β-diacetoxy-5β,20-epoxy-9-oxo-1β,7β,13α-trihydroxy-11-taxene (baccatin III) may be prepared in the following manner:

182 g of triethylsilyl chloride are added over 1 hour 20 minutes to a solution of 293.9 g of 10-deacetylbaccatin III in 2.7 liters of pyridine. The solution obtained is stirred for 40 hours at 5° C. 360 g of acetic anhydride are then added while the temperature is maintained at 5° C. The suspension obtained is stirred for 48 hours at 20° C. and then poured into 40 liters of ice-cold water. The precipitate obtained is separated by filtration, then washed with 8 times 2 liters of water and lastly dissolved in 3 liters of ethyl acetate. The organic phase is dried over magnesium sulphate. After filtration and concentration under reduced pressure, the product obtained is crystallized in isopropyl ether. 7-(Triethylsilyl)baccatin III is thereby obtained in a 77% yield, the characteristics of which product are as follows:

melting point: 254° C.

proton nuclear magnetic resonance spectrum (400 MHz; CDCl$_3$; δ in ppm): 0.58 (mt, 6H: ethyl CH$_2$); 0.92 (t, J=7.5 Hz, 9H: ethyl CH$_3$); 1.02 (s, 3H: CH$_3$); 1.18 (s, 3H: CH$_3$); 1.68 (s, 3H: CH$_3$); 1.75 (broad s, 1H: OH at position 1); 1.87 and 2.53 (2 mt, 1H each: CH$_2$ at position 6); 2.18 (s, 6H: CH$_3$ and COCH$_3$); 2.27 (mt, 2H: CH$_2$ at position 14); 2.28 (s, 3H: COCH$_3$); 2.47 (broad s, 1H: OH at position 13); 3.88 (d, J=7 Hz, 1H: H 3); 4.13 and 4.30 (2d, J=8.5 Hz, 1H each: CH$_2$ at position 20); 4.50 (dd, J=11 and 7 Hz, 1H: H at position 7); 4.81 (mt, 1H: H at position 13); 4.95 (broad d, J=10 Hz, 1H: H at position 5); 5.63 (d, J=7 Hz, 1H: H 2); 6.46 (s, 1H: H at position 10); 7.46 (t, J=8.5 Hz, 2H: —OCOC$_6$H$_5$ H at the meta position); 7.60 (t, J=8.5 Hz, 1H; —OCOC$_6$H$_5$ H at the para position); 8.10 (d, J=8.5 Hz, 2H: —OCOC$_6$H$_5$ H at the ortho position).

2.3 g of trifluoroacetic acid are added to a solution of 350 mg of 7-(triethylsilyl)baccatin III in 3 cm³ of acetonitrile and 2.4 cm³ of pyridine. The reaction mixture is stirred for 48 hours at 50° C. After cooling, it is taken up with 50 cm³ of methylene chloride, washed with twice 5 cm³ of distilled water, 10 cm³ of N hydrochloric acid and twice 5 cm³ of distilled water and dried over magnesium sulphate. After filtration and concentration to dryness under reduced pressure, 330 mg of a product are obtained, which product is purified by chromatography on 30 g of silica contained in a column 2 cm in diameter, eluting with a methylene chloride/methanol (99:1 by volume) mixture. The first 300 cm³ eluted are discarded. The next 275 cm³ yield, after concentration to dryness, 235 mg of baccatin III in the form of a white foam. The yield is 83%.

EXAMPLE 2

Working as in Example 1, but starting from 270 mg of 4α-acetoxy-2α-benzoyloxy-1β,10β-dihydroxy-5β,20- epoxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate and 46 mg of 2-thiophenecarboxylic acid, 230 mg of 4α-acetoxy-2α-benzoyloxy-5β,20-epoxy-1β-hydroxy-7β,8β-methylene-9-oxo-10β-(2-thienylcarbonyl)oxy-19-nor-11-taxen-13α-yl (2R,4S,5R)-3-tert-butoxycarbonyl-2-(4-methoxyphenyl)-4-phenyl-1,3-oxazolidine-5-carboxylate are obtained in the form of a white foam.

Working as in Example 1, but starting from 225 mg of 4α-acetoxy-2α-benzoyloxy-5β,20-epoxy-1β-hydroxy-7β,8β-methylene-9-oxo-10β-(2-thienylcarbonyl)oxy-19-nor-11-taxen-13α-yl (2R,4S,5R)-3-tert-butoxycarbonyl-2-(4-methoxyphenyl)-4-phenyl-1,3-oxazolidine-5-carboxylate, 151 mg of 4α-acetoxy-2α-benzoyloxy-5β,20-epoxy-1β-hydroxy-7β,8β-methylene-9-oxo-10β-(2-thienylcarbonyl)oxy-19-nor-11-taxen-13α-yl (2R,3S)-3-tert-butoxycarbonylamino-2-hydroxy-3-phenylpropionate are obtained in the form of a white foam, the characteristics of which are as follows:

optical rotation: $[\alpha]_{20}^{D}$=−23 (c=0.5; methanol)

$^1$H NMR spectrum (300 MHz; CDCl$_3$; chemical shifts δ in ppm; coupling constants J in Hz); 1.27 (s, 9H: —C(CH$_3$)$_3$); 1.32 (s, 3H: —CH$_3$ at position 16 or at position 17); 1.39 (s, 3H: —CH$_3$ at position 16 or at position 17); 1.43 (mt,1H: —H at position 7); 1.70 and 2.27 (respectively dd and mt, J=6.5 and 5, 1H each: —CH$_2$— at position 19); 1.89 (s, 1H: —OH at position 1); 1.91 (s, 3H: CH$_3$); 2.13 and 2.48 (respectively broad d and dt, J=16 and J=16 and 4.5, 1H each: —CH$_2$ at position 6); 2.25 and 2.39 (respectively dd and mt, J=15.5 and 9, 1H each: —CH$_2$ at position 14); 2.39 (s, 3H: —COCH$_3$); 3.28 (mt, 1H: —OH at position 2'); 4.05 and 4.33 (2 d, J=9, 1H each; —CH$_2$ at position 20); 4.14 (d, J=7.5, 1H; —H at position 3); 4.62 (mt, 1H: —H at position 2'); 4.75 (d, J=4.5, 1H: —H at position 5); 5.28 (broad d, J=10, 1H: —H at position 340); 5.37 (d, J=10 1H: —CONH—); 5.72 (d, J=7.5, 1H: —H at position 2); 6.30 (broad t, J=9, 1H: —H at position 13); 6.52 (s, 1H: —H at position 10); 7.15 [(dd, J=5 and 3.5, 1H: —C$_4$H$_3$S (—H position 4); from 7.25 to 7.45 (mt, 5H: —C$_4$H$_5$ at position 3'); 7.51 [(t, J=7.5, 2H: OCOC$_6$H$_5$ (—H at position 3 and H at position 5)]; 7.61 [(t, J=7.5, 1H: OCOC$_6$H$_5$ (—H at position 4)]; 7.62 [(dd, J=5 and 1.5, 1H: —C$_4$H$_3$S (—H at position 5)]; 7.88 [(dd, J=3.5 and 1.5, 1H: —C$_4$H$_3$S (—H at position 3)]; 8.15 (d, J=7.5, 2H: OCOC$_6$H$_5$ (—H at position 2 and H at position 6).

EXAMPLE 3

Working as in Example 1, but starting from 270 mg of 4α-acetoxy-2α-benzoyloxy-1β,10β-dihydroxy-5β,20epoxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate and 0.038 cm$^3$ of cyclopentanecarboxylic acid, 187 mg of 4α-acetoxy-2α-benzoyloxy-10β-cyclopentylcarbonyloxy-5β,20-epoxy-1β-hydroxy-7β-8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate are obtained in phenyl-1,3-oxazolidine-5-carboxylate are obtained in the form of a white foam.

Working as in Example 1, but starting from 182 mg of 4α-acetoxy-2α-benzoyloxy-10β-cyclopentylcarbonyloxy-5β,20-epoxy-1β-hydroxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate, 100 mg of 4α-acetoxy-2α-benzoyloxy-10β-cyclopentylcarbonyloxy-5β,20-epoxy-1β-hydroxy-7β,8β-methylene-9-oxo-19-nor-11-taxen-13α-yl (2R,3S)-3-tert-butoxycarbonylamino-2-hydroxy-3-phenylpropionate are obtained in the form of a white foam, the characteristics of which are as follows:

optical rotation: $[\alpha]_{20}^{D}$=−40 (c=0.5; methanol)

$^1$H NMR spectrum (300 MHz; CDCl$_3$; chemical shifts δ in ppm; coupling constants J in Hz): 1.26 (s, 3H: —CH$_3$ at position 16 or at position 17); 1.29 (s, 3H: —CH$_3$ at position 16 or at position 17); 1.29 (s, 9H: —C(CH$_3$); 1.40 (mt, 1H: —H at position 7); from 1.50 to 1.80 [(mt, 4H: —C$_5$H$_9$ (—CH$_2$ at position 3 and —CH$_2$ at position 4) and 1H —CH$_2$ at position 19)]; 1.86 (s, 4H: —CH$_3$ and —OH at position 1); from 1.85 to 2.05 [(mt, 4H: —C$_5$H$_9$ (—CH$_2$ at position 2 and —CH$_2$ at position 5)]; 2.11 and 2.47 (respectively broad d and dt, J=16 and J=16 and 4.5, 1H each: —CH$_2$— at position 6); 2.22 and 2.38 (respectively dd and mt, J=15.5 and 9, 1H each: —CH$_2$— at position 14); 2.25 (mt, 1H: —CH$_2$ at position 19); 2.39 (s, 3H: —COCH$_3$); 2.90 (mt, 1H: —C$_5$H$_9$ (—CH< at position 1)]; 3.26 (mt, 1H: —OH at position 2'); 4.03 and 4.31 (2 d, J=9,1H each: —CH$_2$ at position 20); 4.11 (d, J=7.5, 1H: —H at position 3); 4.62 (mt, 1H: H at position 2'); 4.74 (d, J=4.5, 1H: —H at position 5); 5.28 (broad d, J=10, 1H: —H at position 3'); 5.35 (d, J=10, 1H: —CONH—); 5.68 (d, J=7.5, 1H: —H at position 2); 6.27 (broad t, J=9, 1H: —H at position 13); 6.32 (s, 1H: —H at position 10); from 7.25 to 7.45 (mt, 5H: —C$_6$H$_5$ at position 3'); 7.51 [(t, J=7.5, 2H: —OCOC$_6$H$_5$ (—H at position 3 and H at position 5)]; 7.60 [(t, J=7.5, 1H: —OCOC$_6$H$_5$ (—H at position 4)]; 8.15 (d, J=7.5, 2H: —OCOC$_6$H$_5$ (—H at position 2 and H at position 6)].

EXAMPLE 4

Working as in Example 1, but starting from 270 mg of 4α-acetoxy-2α-benzoyloxy-1β,10β-dihydroxy-5β,20-epoxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate and 0.028 cm$^3$ of cyclopropanecarboxylic acid, 110 mg of 4α-acetoxy-2α-benzoyloxy-10β-cyclopropylcarbonyloxy-5β,20-epoxy-1β-hydroxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate are obtained in the form of a white foam.

Working as in Example 1, but starting from 110 mg of 4α-acetoxy-2α-benzoyloxy-10β-cyclopropylcarbonyloxy-5β,20-epoxy-1β-hydroxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate, 62 mg of 4α-acetoxy-2α-benzoyloxy-10β-cyclopropylcarbonyloxy-5β,20-epoxy-1β-hydroxy-7β,8β-methylene-9-oxo-19-nor-11-taxen-13α-yl (2R,3S)-3-tert-butoxycarbonylamino-2-hydroxy-3-phenylpropionate are obtained in the form of a white foam, the characteristics of which are as follows:

optical rotation: $[\alpha]_{20}^{D}$=−35 (c=0.5; methanol)

$^1$H NMR spectrum (400 MHz; CDCl$_3$; chemical shifts δ in ppm; coupling constants J in Hz): 0.98 and 1.13 (2 mt, 2H each: —C$_3$H$_5$ (—CH$_2$— at position 2 and —CH$_2$— at position 3); 1.27 (s, 3H: —CH$_3$ at position 16 or at position 17); 1.30 (s, 12H: —CH$_3$ at position 16 or at position 17 and —C(CH$_3$)$_3$); 1.38 (mt, 1H: —H at position 7); 1.67 and 2.26 (respectively dd and mt, J=6.5 and 5, 1H each: —CH$_2$— at position 19); 1.74 (mt, 1H: —C$_3$H$_5$ (—CH< at position 1); 1.86 (s, 4H: —OH at position 1 and —CH$_3$); 2.12 and 2.44 (respectively broad d and dt, J=16 and J=16 and 4.5, 1H each: —CH$_2$— at position 6); 2.25 and 2.38 (respectively dd and mt, J=16 and 9, 1H each: —CH$_2$— at position 14); 2.38 (s, 3H: —COCH$_3$); 3.27 (mt, 1H: —OH at position 2'); 4.03 and 4.32 (2 d, J=9, 1H each: —CH$_2$— at position 20); 4.10 (d, J=7.5, 1H: —H at position 3); 4.62 (mt, 1H: —H at position 2'); 4.72 (d, J=4.5, 1H: —H at position 5); 5.29 (broad d, J=10, 1H: —H at position 3'); 5.36 (d, J=10, 1H: —CONH—); 5.67 (d, J=7.5;1H: —H at position 2); 6.28 (broad t, J=9, 1H: —H at position 13); 6.34 (s, 1H: —H at position 10); from 7.25 to 7.45 (mt, 5H: —C$_6$H$_5$ at position 3'); 7.51 [(t, J=7.5, 2H: —OCOC$_6$H$_5$ (—H at position 3 and H at position 5)]; 7.61 [(t, J=7.5, 1H: —OCOC$_6$H$_5$ (—H at position 4)]; 8.15 [(d, J=7.5, 2H: —OCOC$_6$H$_5$ (—H at position 2 and H at position 6)].

EXAMPLE 5

Working as in Example 1, but starting from 280 mg of 4α-acetoxy-2α-benzoyloxy-1β,10β-dihydroxy-5β,20-epoxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate and 41.5 mg of 2-furancarboxylic acid, 201 mg of 4α-acetoxy-2α-benzoyloxy-5β,20-epoxy-10β-(2-furylcarbonyl)oxy-1β-hydroxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate are obtained in the form of a white foam.

Working as in Example 1, but starting from 197 mg of 4α-acetoxy-2α-benzoyloxy-5β,20-epoxy-10β-(2-furylcarbonyl)oxy-1β-hydroxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate, 137 mg of 4α-acetoxy-2α-benzoyloxy-5β,20-epoxy-10β-(2-furylcarbonyl)oxy-1β-hydroxy-7β,8β-methylene-9-oxo-19-nor-11-taxen-13α-yl (2R,3S)-3-tert-butoxycarbonylamino-2-hydroxy-3-phenylpropionate are obtained in the form of a white foam, the characteristics of which are as follows:

optical rotation: $[\alpha]_{20}^{D}$=−19 (c=0.5; methanol)

$^1$H NMR spectrum (400 MHz; CDCl$_3$; chemical shifts δ in ppm; coupling constants J in Hz): 1.28 (s, 9H: —C(CH$_3$)$_3$); 1.32 (s, 3H: —CH$_3$ at position 16 or at position 17); 1.38 (m, 3H: —CH$_3$ at position 16 or at position 17); 1.43 (mt, 1H: —H at position 7); 1.70 and 2.28 (respectively dd and mt, J=7 and 5, 1H each: —CH$_2$— at position 19); 1.89 (s, 1H: —OH at position 1); 1.91 (s, 3H: —CH$_3$); 2.12 and 2.49 (respectively broad d and d, J=16 and J=16 and 4.5, 1H each: —CH$_2$— at position 6); 2.27 and 2.40 (respectively dd and mt, J=16 and 9, 1H each: —CH$_2$— at position 14); 2.40 (s, 3H: —COCH$_3$); 3.26 (mt, 1H: —OH at position 2'); 4.05 and 4.33) (2 d, J=9, 1H each: —CH$_2$— at position 20); 4.10 (d, J=7.5, 1H: —H 3); 4.63 (mt, 1H: H at position 2'); 4.72 (d, J=4.5, 1H: —H at position 5); 5.29 (broad d, J=10, 1H: —H at position 3'); 5.36 (d, J=10, 1H: —CONH—); 5.71 (d, J=7.5, 1H: —H at position 2H); 6.29 (broad t, J=9 1H: —H at position 13); 6.53 (s, 1H: —H at position 10); 6.56 [(dd, J=5 and 1.5, 1H: —C$_4$H$_3$O (—H at position 4)]; 7.26 [(d, J=4, 1H: —C$_4$H$_3$O (—H at position 3)]; from 7.25 to 7.45 (mt, 5H: —C$_6$H$_5$ at position 3'); 7.51 (t, J=7.5, 2H: —OCOC$_6$H$_5$ (—H at position 3 and H at position 5)]; 7.61 (t, J=7.5, 1H: —OCOC$_6$H$_5$ (—H at position 4)]; 7.64 (broad s, 1H: —C$_4$H$_3$O (—H at position 5)]; 8.15 (d, J=7.5, 2H: —OCOC$_6$H$_5$ (—H at position 2 and H at position 6)].

EXAMPLE 6

Working as in Example 1, but starting from 280 mg of 4α-acetoxy-2α-benzoyloxy-1β,10β-dihydroxy-5β,20-epoxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate and 45 mg of benzoic acid, 190 mg of 4α-acetoxy-2α,10β-dibenzoyloxy-5β,20-epoxy-1β-hydroxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate are obtained in the form of a white foam.

Working as in Example 1, but starting from 190 mg of 4α-acetoxy-2α,10β-dibenzoyloxy-5β,20-epoxy-1β-hydroxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate, 120 mg of 4α-acetoxy-2α,10β-dibenzoyloxy-5β,20-epoxy-1β-hydroxy-7β,8β-methylene-9-oxo-19-nor-11-taxen-13α-yl (2R,3S)-3-tert-butoxycarbonylamino-2-hydroxy-3-phenylpropionate are obtained in the form of a white foam, the characteristics of which are as follows:

optical rotation: $[\alpha]_{20}^{D}$=−28 (c=0.5; methanol)

$^1$H NMR spectrum (400 MHz; CDCl$_3$; chemical shifts δ in ppm; coupling constants J in Hz): 1.29 (s, 9H: —C(CH$_3$)$_3$); 1.34 (s, 3H: —CH$_3$ at position 16 or at position 17); 1.42 (s, 3H: —CH$_3$ at position 16 or at position 17); 1.42 (mt, 1H: —H at position 7); 1.69 and 2.27 (respectively dd and mt, J=7 and 5, 1H each: —CH$_2$ at position 19); 1.91 (s, 1H: —OH at position 1); 1.92 (s, 3H: —CH$_3$); 2.13 and 2.50 (respectively broad d and dt, J=16 and J=16 and 4.5, 1H each: —CH$_2$— at position 6); 2.26 and 2.41 (respectively dd and mt, J=16 and 9, 1H each: —CH$_2$— at position 14); 2.41 (s, 3H: —COCH$_3$); 3.26 (mt,1H: —OH at position 2'); 4.07 and 4.34 (2 d, J=9, 1H each: —CH$_2$— at position 20); 4.18 (d, J=7.5, 1H: —H at position 3); 4.63 (mt, 1H: —H at position 2'); 4.75 (d, J=4.5, 1H: —H at position 5); 5.29 (broad d, J=10, 1H: —H at position 3'); 5.37 (d, J=10, 1H: —CONH—); 5.73 (d, J=7.5, 1H: —H at position 2H); 6.29 (broad t, J=9, 1H: —H at position 13); 6.60 (s, 1H: —H at position 10); from 7.25 to 7.45 (mt, 5H: —C$_6$H$_5$ at position 3'); 7.49 and 7.51 [(2 t, J=7.5, 2H each: —OCOC$_6$H$_5$ (—H at position 3 and H at position 5)]; from 7.55 to 7.65 [(mt, 2H: —OCOC$_6$H$_5$ (—H at position 4)]; 8.09 and 8.17 [(2 d, J=7.5, 2H each: —OCOC$_6$H$_5$ (—H at position 2 and H at position 6)].

EXAMPLE 7

Working as in Example 1, but starting from 300 mg of 4α-acetoxy-2α-benzoyloxy-1β,10β-dihydroxy-5β,20-epoxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate and 0.686 cm$^3$ of 3-methyl-2-propenoic anhydride, 237 mg of 4α-acetoxy-2α-benzoyloxy-5β,20-epoxy-1β-hydroxy-10β-(3-methyl-2-propenoyl)oxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate are obtained in the form of a white foam.

Working as in Example 1, but starting from 270 mg of 4α-acetoxy-2α-benzoyloxy-5β,20-epoxy-1β-hydroxy-10β-(3-methyl-2-propenoyl)oxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate, 192 mg of 4α-acetoxy-2α-benzoyloxy-5β,20-epoxy-1β-hydroxy-10β-(3-methyl-2-propenoyl)oxy-7β,8β-methylene-9-oxo-19-nor-11-taxen-13α-yl (2R,3S)-3-tert-butoxycarbonylamino-2-hydroxy-3-phenylpropionate are obtained in the form of a white foam, the characteristics of which are as follows:

optical rotation: $[\alpha]_{20}^D$=−34 (c=0.5; methanol)

$^1$H NMR spectrum (400 MHz; CDCl$_3$; chemical shifts δ in ppm; coupling constants J in Hz): 1.27 (s, 12H: —C(CH$_3$)$_3$ and —CH$_3$ at position 16 or at position 17); 1.30 (s, 3H: —CH$_3$ at position 16 or at position 17); 1.39 (mt, 1H: —H at position 7); 1.67 and 2.26 (respectively dd and mt, J=6.5 and 5.5, 1H each: —CH$_2$ at position 19); 1.86 (s, 4H: —OH at position 1 and —CH$_3$); 1.93 (dd, J=7.5 and 1.5, 3H: —CH$_3$); 2.11 and 2.47 (respectively broad d and dt, J=16 and J=16 and 4.5, 1H each: —CH$_2$— at position 6); 2.23 and 2.39 (respectively dd and mt, J=16 and 9, 1H each: —CH$_2$— at position 14); 2.38 (s, 3H: —COCH$_3$); 3.25 (mt, 1H: —OH at position 2'); 4.04 and 4.30 (2 d, J=9, 1H each: —CH$_2$— at position 20); 4.12 (d, J=7.5,1H: —H at position 3); 4.62 (mt, 1H: —H at position 2'); 4.73 (d, J=4.5, 1H: —H at position 5); 5.29 (broad d, J=10, 1H: —H at position 3') 5.36 (d, J=10, 1H: —CONH—); 5.68 (d, J=7.5, 1H: —H at position 2); 5.98 [(dd, J=16 and 1.5, 1H: —OCOCH=CH—CH$_3$)]; 6.27 (broad t, J=9, 1H: —H at position 13); 6.40 (s, 1H: —H at position 10); 7.07 [(dt, J=16 and 7.5, 1H: —OCOCH=CH—CH$_3$)]; from 7.25 to 7.50 (mt, 5H: —C$_6$H$_5$ at position 3'); 7.51 [(t, J=7.5, 2H: OCOC$_6$H$_5$ (—H at position 3 and H at position 5)]; 7.61 [(t, J=7.5, 1H: —OCOC$_6$H$_5$ (—H at position 4)]; 8.15 [(d, J=7.5, 2H: OCOC$_6$H$_5$ (—H at position 2 and H at position 6)].

EXAMPLE 8

Working as in Example 1, but starting from 220 mg of 4α-acetoxy-2α-benzoyloxy-1β,10β-dihydroxy-5β,20-epoxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate and 28 mg of chloroacetic acid, 100 mg of 4α-acetoxy-2α-benzoyloxy-10β-chloroacetoxy-5β,20-epoxy-1β-hydroxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate are obtained in the form of a white foam.

Working as in Example 1, but starting from 155 mg of 4α-acetoxy-2α-benzoyloxy-10β-chloroacetoxy-5β,20-epoxy-1β-hydroxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate, 64 mg of 4α-acetoxy-2α-benzoyloxy-10β-chloroacetoxy-5β,20-epoxy-1β-hydroxy-7β,8β-methylene-9-oxo-19-nor-11-taxen-13α-yl (2R,3S)-3-tert-butoxycarbonylamino-2-hydroxy-3-phenylpropionate are obtained in the form of a white foam, the characteristics of which are as follows:

optical rotation: $[\alpha]_{20}^D$=−39 (c=0.5; methanol)

$^1$H NMR spectrum (400 MHz; CDCl$_3$; chemical shifts δ in ppm; coupling constants J in Hz): 1.27 (s, 3H: —CH$_3$ at position 16 or at position 17); 1.29 (s, 12H: —CH$_3$ at position 16 or at position 17 and —C(CH$_3$)$_3$; 1.39 (mt, 1H: —H at position 7); 1.71 and 2.26 (respectively dd and mt, J=7 and 5.5, 1H each: —CH$_2$— at position 19); 1.87 (s, 4H: —OH at position 1 and —CH$_3$); 2.12 and 2.47 (respectively broad d and dt, J=16 and J=16 and 4.5, 1H each: —CH$_2$— at position 6); 2.27 and 2.38 (respectively dd and mt, J=16 and 9, 1H each: —CH$_2$— at position 14); 2.40 (s, 3H: —COCH$_3$); 3.27 (mt, 1H: —OH at position 2'); 4.03 and 4.32 (2 d, J=9, 1H each: —CH$_2$— at position 20); 4.07 (d, J=7.5, 1H: —H at position 3); 4.26 (limiting AB, J=16, 2H: —OCOCH$_2$Cl); 4.62 (mt, 1H: —H at position 2'); 4.74 (d, J=4.5, 1H: —H at position 5); 5.28 (broad d, J=10 Hz, 1H: —H at position 3'); 5.35 (d, J=10, 1H: —CONH—); 5.68 (d, J=7.5, 1H: —H2); 6.28 (broad t, J=9 Hz, 1: —H at position 13); 6.38 (s,1H: —H at position 10); from 7.25 to 7.45 (mt, 5H: —C$_6$H$_5$ at position 3'); 7.51 [(t, J=7.5, 2H: —OCOC$_6$H$_5$ (—H at position 3 and H at position 5)]; 7.61 [(t, J=7.5, 1H: —OCOC$_6$H$_5$ (—H at position 4)]; 8.16 (d, J=7.5, 2H: —OCOC$_6$H$_5$ (—H at position 2 and H at position 6)].

EXAMPLE 9

Working as in Example 7, but starting from 300 mg of 4α-acetoxy-2α-benzoyloxy-1β,10β-dihydroxy-5β,20-epoxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate and 52.4 mg of ethoxycarbonylacetic acid, 180 mg of 4α-acetoxy-2α-benzoyloxy-5β,20-epoxy-10β-ethoxycarbonylacetoxy-1β-hydroxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate are obtained in the form of a white foam.

Working as in Example 7, but starting from 190 mg of 4α-acetoxy-2α-benzoyloxy-5β,20-epoxy-10β-ethoxycarbonylacetoxy-1β-hydroxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate, 73 mg of 4α-acetoxy-2α-benzoyloxy-5β,20-epoxy-10β-ethoxycarbonylacetoxy-1β-hydroxy-7β,8β-methylene-9-oxo-19-nor-11-taxen-13α-yl (2R,3S)-3-tert-butoxycarbonylamino-2-hydroxy-3-phenylpropionate are obtained in the form of a white foam, the characteristics of which are as follows:

optical rotation: $[\alpha]_{20}^D$=−28 (c=0.5; methanol)

$^1$H NMR spectrum (300 MHz; CDCl$_3$; chemical shifts δ in ppm; coupling constants J in Hz): 1.24 (s, 3H: —CH$_3$ at position 16 or at position 17); 1.28 (s, 12H: —C(CH$_3$)$_3$ and —CH$_3$ at position 16 or at position 17); 1.32 (t, J=7.5, 3H: —OCOCH$_2$COOCH$_2$CH$_3$); 1.41 (mt, 1H: —H at position 7); 1.72 and 2.22 (respectively dd and mt, J=6.5 and 5, 1H each: —CH$_2$— at position 19); 1.89 (s, 4H: —OH at position 1 and —CH$_3$); 2.15 and 2.50 (respectively broad d and dt, J=16 and J=16 and 4.5, 1H each: —CH$_2$— at position 6); 2.28 and 2.40 (respectively dd and mt, J=16 and 9, 1H each: —CH$_2$— at position 14); 2.42 (s, 3H: —COCH$_3$); 3.32 (mt, 1H: —OH at position 2'); 3.58 (limiting AB, 2H: —OCOCH$_2$COOCH$_2$CH$_3$); 4.08 and 4.35 (2 d, J=9 Hz, 1H each: —CH$_2$— at position 20); 4.10 (d, J=7.5, 1H: —H at position 3); 4.28 (q, J=7.5, 2H: —OCOCH$_2$COOCH$_2$CH$_3$); 4.63 (mt, 1H: —H at position 2'); 4.75 (d, J=4.5, 1H: —H at position 5); 5.29 broad d, J=10, 1H: —H at position 3'); 5.39 (d, J=10, 1H: —CONH—); 5.69 (d, J=7.5, 1H: H at position 2); 6.30 (broad t, J=9, 1H: —H at position 13); 6.38 (s, 1H: —H at position 10); from 7.25 to 7.50 (mt, 5H: —C$_6$H$_5$ at position 3'); 7.53 [(t, J=7.5, 2H: —OCOC$_6$H$_5$ (—H at position 3 and H at position 5)]; 7.62 [(t, J=7.5, 1H: —OCOC$_6$H$_5$ (—H at position 4)]; 8.18 [(d, J=7.5, 2H: —OCOC$_6$H$_5$ (—H at position 2 and H— at position 6)].

EXAMPLE 10

Working as in Example 1, but starting from 4α-acetoxy-2α-benzoyloxy-1β,10β-dihydroxy-5β,20-epoxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate and 584 mg of acrylic anhydride, 160 mg of 4α-acetoxy-10β-acryloyloxy-2α-benzoyloxy-5β,20-epoxy-1β-hydroxy-7β,8β-methylene-9-oxo-19-nor-11-taxen-13α-yl (2R,4S,5R)-3-tert-butoxycarbonyl-2-(4- methoxyphenyl)-4-phenyl-1,3-oxazolidine-5-carboxylate are obtained in the form of a white foam.

Working as in Example 1, but starting from 196 mg of 4α-acetoxy-10β-acryloyloxy-2α-benzoyloxy-5β,20-epoxy-1β-hydroxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate, 113 mg of 4α-acetoxy-10β-acryloyloxy-2α-benzoyloxy-5β,20-epoxy-1β-hydroxy-7β,8β-methylene-9-oxo-19-nor-11-taxen-13α-yl (2R,3S)-3-tert-butoxycarbonylamino-2-hydroxy-3-phenylpropionate are obtained in the form of a white foam, the characteristics of which are as follows:

optical rotation: $[\alpha]_{20}^{D} = -39$ (c=0.5; methanol)

$^1$H NMR spectrum (400 MHz; CDCl$_3$; chemical shifts δ in ppm; coupling constants J in Hz): 1.27 [s, 12H: —C(CH$_3$)3 and CH$_3$ at position 16 or at position 17]; 1.30 (s, 3H: —CH$_3$ at position 16 or at position 17); 1.39 (mt, 1H: —H at position 7); 1.68 and 2.26 (respectively dd and mt, J=6.5 and 5, 1H each: —CH$_2$— at position 19); 1.86 (s, 1H: —OH 1); 1.88 (s, 3H: —CH$_3$); 2.13 and 2.49 (respectively broad d and dt, J=15 and J=15 and 4, 1H each: —CH$_2$— at position 6); 2.25 and 2.39 (2 mts, 1H each: —CH$_2$— at position 14); 2.38 (s, 3H: —COCH$_3$); 3.27 (mt, 1H: —OH at position 2'); 4.06 and 4.34 (2 d, J=9, 1H each): —CH$_2$— at position 20); 4.13 (d, J=7, 1H: —H at position 3); 4.63 (mt, 1H: —H at position 2'); 4.75 (d, J=4, 1H: —H at position 5); 5.29 (broad d, J=10, 1H: —H at position 3'); 5.35 (d, J=10, 1H: —CONH—); 5.69 (d, J=7, 1H: —H at position 2); 5.95 and 6.53 (2 dd, respectively J=10 and 1.5 and J=16 and 1.5, 1H each: —OCOCH=CH$_2$); 6.27 (dd, J=16 and 10, 1H: —OCOCH=CH$_2$); 6.29 (mt, 1H: —H at position 13); 6.42 (s, 1H: —H at position 10); from 7.25 to 7.45 (mt, 5H: —C$_6$H$_5$ at position 3'); 7.53 [(t, J=7.5, 2H: —OCOC$_6$H$_5$ (—H at position 3 and H at position 5)]; 7.63 [(t, J=7.5, 1H: —OCOC$_6$H$_5$ (—H at position 4)]; 8.17 (d, J=7.5, 2H: —OCOC$_6$H$_5$ (—H at position 2 and H— at position 6)].

EXAMPLE 11

Working as in Example 1, but starting from 250 mg of 4α-acetoxy-2α-benzoyloxy-1β,10β-dihydroxy-5β,20-epoxy-7β,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate and 41 mg of 3-pyridinecarboxylic acid, 269 mg of 4α-acetoxy-2α-benzoyloxy-5β,20-epoxy-1β-hydroxy-7β,8β-methylene-9-oxo-10β-(3-pyridylcarbonyl)oxy-19-nor-11-taxen-13α-yl (2R,4S,5R)-3-tert-butoxycarbonyl-2-(4-methoxyphenyl)-4-phenyl-1,3-oxazolidine-5-carboxylate are obtained in the form of a white foam.

Working as in Example 1, but starting from 264 mg of 4α-acetoxy-2α-benzoyloxy-5β,20-epoxy-1β-hydroxy-7β,8β-methylene-9-oxo-10β-(3-pyridylcarbonyl)oxy-19-nor-11-taxen-13α-yl (2R,4S,5R)-3-tert-butoxycarbonyl-2-(4-methoxyphenyl)-4-phenyl-1,3-oxazolidine-5-carboxylate, 169 mg of 4α-acetoxy-2α-benzoyloxy-5β,20-epoxy-1β-hydroxy-7β,8β-methylene-9-oxo-10β-(3-pyridylcarbonyl)oxy-19-nor-11-taxen-13α-yl (2R,3S)-3-tert-butoxycarbonylamino-2-hydroxy-3-phenylpropionate are obtained in the form of a white foam, the characteristics of which are as follows:

optical rotation: $[\alpha]_{20}^{D} = -25$ (c=0.5; methanol)

$^1$H NMR spectrum (400 MHz; CDCl$_3$; chemical shifts δ in ppm; coupling constants J in Hz): 1.29 [s, 9H: —C(CH$_3$)3]; 1.34 (s, 3H: —CH$_3$ at position 16 or at position 17); 1.41 (s, 3H: —CH$_3$ at position 16 or at position 17); 1.45 (mt, 1H: —H at position 7); 1.74 and 2.29 (respectively dd and mt, J=6.5 and 5,5, 1H each: —CH$_2$— at position 19); 1.94 (s, 3H: —CH$_3$); 2.14 and 2.52 (respectively broad d and dt, J=16 and J=16 and 4, 1H each: —CH$_2$— at position 6); 2.29 and 2.43 (2 mts, 1H each: —CH$_2$— at position 14); 2.43 (s, 3H: —COCH$_3$); 3.31 (mt, 1H: —OH at position 2'); 4.07 and 4.35 (2 d, J=9, 1H each: —CH$_2$— at position 20); 4.17 (d, J=7.5, 1H: —H at position 3); 4.64 (mt, 1H: —H at position 2'); 4.77 (d, J=4, 1H: —H at position 5); 5.30 (broad d, J=10, 1H: —H at position 3'); 5.37 (d, J=10, 1H: —CONH—); 5.74 (d, J=7.5, 1H: —H at position 2); 6.32 (broad t, J=8.5, 1H: —H at position 13); 6.63 (s, 1H: —H at position 10); from 7.25 to 7.45 (mt, 5H: —C$_6$H$_5$ at position 3'); 7.45 [(dd, J=8 and 5.5, 1H: —OCOC$_5$H$_4$N (—H at position 5)]; 7.53 [(t, J=7.5, 2H: —OCOC$_5$H$_5$ (—H at position 3 and H at position 5)]; 7.63 [(t, J=7.5, 1H: —OCOC$_6$H$_5$ (—H at position 4)]; 8.18 [(d, J=7.5, 2H: —OCOC$_6$H$_5$ (—H at position 2 and —H at position 6)]; 8.36 [(dt, J=8 and 1.5, 1H: —OCOC$_5$H$_4$N (—H at position 4)]; 8.84 (dd, J=5.5 and 1.5, 1H: —OCOC$_5$H$_4$N (—H at position 6)]; 9.29 (d, J=1.5, 1H: —OCOC$_5$H$_4$N (—H at position 2)].

EXAMPLE 12

Working as in Example 1, but starting from 250 mg of 4α-acetoxy-2α-benzoyloxy-1β,10β-dihydroxy-5β,20-epoxy-7β,8β-methylene-9-oxo-19nor-11-taxen-13α-yl (2R, 4S, 5R)-3-tert-butoxycarbonyl-2-(4-methoxy-phenyl)-4phenyl-1,3-oxazolidine-5-carboxylate and 42 mg of 3-thiophenecarboxylic acid, 180 mg of 4α-acetoxy-2α-benzoyloxy-5β,20-epoxy-1β-hydroxy-7β,8β-methylene-9-oxo-10β-(3-thenoyl)oxy-19-nor-11-taxen-13α-yl (2R, 4S, 5R)-3-tert-butoxycarbonyl-2-(4-methoxy-phenyl)-4-phenyl-1,3-oxazolidine-5-carboxylate are obtained in the form of a white foam.

Working as in Example 1, but starting from 175 mg of 4α-acetoxy-2β0-benzoyloxy-5β,20-opoxy-1β2-hydroxy-7β,8β-methylene-9-oxo-10β-(3-thenoyl)oxy-19-nor-11-taxen-13α-yl (2R, 4S, 5R)-3-tert-butoxycarbonyl-2-(4-methoxyphenyl)-4-phenyl-1,3-oxazolidine-5-carboxylate, 102 mg of 4α-acetoxy-2α-benzoyloxy-5β,20-epoxy-1β-hydroxy-7β,8β-methylene-9-oxo-10β-(3-thenoyl)oxy-19nor-11-taxen-13α-yl (2R, 3S)-3-tert-butoxycarbonylamino-2-hydroxy-3-phenylpropionate are obtained in the form of a white foam, the characteristics of which are as follows:

optical rotation: $[\alpha]_{20}^{D} = -16$ (c=0.5; methanol)

$^1$H NMR spectrum (400 MHz; CDCl$_3$; chemical shifts δ in ppm; coupling constants J in Hz): 1.30 [s, 9H: —C(CH$_3$)$_3$]; 1.33 (s, 3H: —CH$_3$ at position 16 or at position 17); 1.40 (s, 3H: —CH$_3$ at position 16 or at position 17); 1.44 (mt, 1H: —H at position 7); 1.72 and 2.29 (2 dd, respectively J=6.5 and 5.5 and J=10 and 6.5, 1H each: —CH$_2$— 19); 1.92 (s, 4H: —CH$_3$ and —OH at position 1); 2.14 and 2.51 (respectively broad d and dt, J=16 and J=16 and 4, 1H each: —CH$_2$— at position 6); 2.26 and 2.42 (2 mts, 1H each: —CH$_2$— at position 14); 2.42 (s, 3H: —COCH$_3$); 3.27 (mt, 1H: —OH at position 2'); 4.06 and 4.32 (2 d, J=9, 1H each: —CH$_2$—at position 20); 4.17 (d, J=7.5, 1H: —H at position 3); 4.63 (mt, 1H: —H at position 2'); 4.76 (d, J=4, 1H: —H at position 5); 5.29 (broad d, J=10, 1H: —H at position 3'); 5.35 (d, J=10, 1H: —CONH—); 5.72 (d, J=7.5, 1H: —H at position 2); 6.30 (broad t, J=8.5, 1H: —H at position 13); 6.53 (s, 1H: —H at position 10); from 7.25 to 7.45 [mt, 6H: —C$_6$H$_5$ at position 3' and —OCOC$_4$H$_3$S (—H at position 5)]; 7.53 [(t, J=7.5, 2H: —OCOC$_6$H$_5$ (—H at position 3 and H at position 5)]; 7.57 [broad d, J=5.5, 1H: —OCOC$_4$H$_3$S (—H at position 4)]; 7.62 [(t, J=7.5, 1H: —OCOC$_6$H$_5$ (—H at position 4)]; 8.17 [(d, J=7.5, 2H: —OCOC$_6$H$_5$ (—H at position 2 and H— at position 6)]; 8.19 [mt, 1H: —OCOC$_4$H$_3$S (—H at position 2)].

EXAMPLE 13

Working as in Example 1, but starting from 300 mg of 4α-acetoxy-2α-benzoyloxy-1β, 10β-dihydroxy-5β, 20β-epoxy-7β,8β-methylene-9-oxo-19-nor-11-taxen-13α-yl (2R, 4S, 5R)-3-tert-butoxycarbonyl-2-(4-methoxy-phenyl)-4-phenyl-1,3-oxazolidine-5-carboxylate and 713 mg of vinylacetic anhydride, 114 mg of 4α-acetoxy-10β-allylcarbonyloxy-2α-benzoyloxy-5β,20-epoxy-1β-hydroxy-7β,8β-methylene-9-oxo-19-nor-11-taxen-13α-yl (2R, 4S, 5R)-3-tert-butoxycarbonyl-2-(4-methoxyphenyl)-4-phenyl-1,3-oxazolidine-5-carboxylate are obtained in the form of a white foam.

Vinylacetic anhydride may be prepared in the following manner:

2.8 cm$^3$ of vinylacetic acid are added dropwise and at a temperature in the region of 20° C. to a solution, maintained under an argon atmosphere and kept stirring, of 3.42 g of N,N'-dicyclohexyl-carbodiimide in 20 cm$^3$ of dichloromethane. The reaction medium is kept stirring at a temperature in the region of 20° C. for 3 days, and then filtered through sintered glass lined with Celite. The sintered glass is washed with twice 10 cm$^3$ of dichloromethane, and the filtrates are combined and concentrated to dryness under reduced pressure (2.7 kPa) at 40° C. 2.96 g of vinylacetic anhydride are thereby obtained in the form of a yellow oil.

Working as in Example 1, but starting from 140 mg of 4α-acetoxy-10β-allylcarbonyloxy-2α-benzoyloxy-5β,20-epoxy-1β-hydroxy-7β,8β-methylene-9-oxo-19-nor-11-taxen-13α-yl (2R, 4S, 5R)-3-tert-butoxycarbonyl-2-(4-methoxyphenyl)-4-phenyl-1,3-oxazolidine-5-carboxylate, 80 mg of 4α-acetoxy-10β-allylcarbonyloxy-2α-benzoyloxy-5β,20-epoxy-1β-hydroxy-7β,8β-methylene-9-oxo-19-nor-11-taxen-13α-yl (2R, 3S)-3-tert-butoxycarbonylamino-2-hydroxy-3-phenylpropionate are obtained in the form of a white foam, the characteristics of which are as follows:

optical rotation: $[α]^D_{20}$=−34 (c=0.5; methanol) —$^1$H NMR spectrum (400 MHz; CDCl$_3$; chemical shifts δ in ppm; coupling constants J in Hz): 1.26 (s, 3H: —CH$_3$ at position 16 or at position 17); 1.29 [s, 12H: —C(CH$_3$)$_3$ and —CH$_3$ at position 16 or at position 17]; 1.38 (mt, 1H: —H at position 7); 1.69 and 2.26 (2 dd, respectively J=6.5 and 5.5 and J=10 and 6.5, 1H each: —CH$_2$— at position 19); 1.84 (s, 1H: —OH at position 1); 1.85 (s, 3H: —CH$_3$); 2.12 and 2.46 (respectively broad d and dt, J=16 and J=16 and 4, 1H each: —CH$_2$—at position 6); 2.24 and 2.40 (2 mts, 1H each: —CH$_2$— at position 14); 2.40 (s, 3H: —COCH$_3$); 3.27 (mt, 3H: —OH at position 2' and OCOCH$_2$—CH=CH$_2$); 4.05 and 4.32 (2 d, J=9, 1H each: —CH$_2$— at position 20); 4.11 (d, J=7.5, 1H: —H at position 3); 4.63 (mt, 1H: —H at position 2'); 4.73 (d, J=4, 1H: —H at position 5); 5.24 and 5.26 (2dd respectively J=8 and 2 and J=18 and 2, 1H each: OCOCH$_2$—CH=CH$_2$);p 5.29 (broad d, J=10, 1H: —H at position 3'); 5.34 (d, J=10, 1H: —CONH—); 5.69 (d, J=7.5, 1H: —H at position 2); 6.00 (mt, 1H: OCOCH$_2$—CH=CH$_2$); 6.28 (broad t, J=8.5, 1H: —H at position 13); 6.34 (s, 1H: —H at position 10); from 7.25 to 7.45 (mt, 5H: —C$_6$H$_5$ at position 3'); 7.53 [(t, J=7.5, 2H: —OCOC$_6$H$_5$ (—H at position 3 and H at position 5)]; 7.62 [(t, J=7.5, 1H: —OCOC$_6$H$_5$ (—H at position 4)]; 8.15 (d, J=7.5, 2H: —OCOC$_6$H$_5$ (—H at position 2 and H— at position 6)].

EXAMPLE 14

Working as in Example 1, but starting from 300 mg of 4α-acetoxy-2α-benzoyloxy-1β,10β-dihydroxy-5β,20-epoxy-7β,8β- methylene-9-oxo-19-nor-11-taxen-13α-yl (2R, 4S, 5R)-3-tert-butoxycarbonyl-2-(4-methoxy-phenyl)-4-phenyl-1,3-oxazolidine-5-carboxylate and 45 mg of 3-furnancarboxylic acid, 282 mg of 4α-acetoxy-2α-benzoyloxy-5β,20-epoxy-10β-(3-furoyl)oxy-1β-hydroxy-7β,8β-methylene-9-oxo-19-nor-11-taxen-13α-yl (2R, 4S, 5R)-3-oxazolidine-5-carboxylate are obtained in the form of a white foam.

Working as in Example 1, but starting from 282 mg of 4α-acetoxy-2α-benzoyloxy-5β,20-epoxy-10β-(3-furoyl)oxy-1β-hydroxy-7β,8β-methylene-9-oxo-19-nor-11-taxen-13α-yl (2R, 4S, 5R)-3-tert-butoxycarbonyl-2-(4-methoxyphenyl)-4-phenyl-1,3-oxazolidine-5-carboxylate, 143 mg of 4α-acetoxy-2α-benzoyloxy-5β,20-epoxy-10β-(3-furoyl)oxy-1β-hydroxy-7β,8β-methylene-9-oxo-19-nor-11-taxen-13α-yl (2R, 3S)-3-tert-butoxycarbonylamino-2-hydroxy-3-phenylpropionate are obtained in the form of a white foam, the characteristics of which are as follows:

optical rotation: $[α]^D_{20}$=−26 (c=0.5; methanol)

$^1$H NMR spectrum (400 MHz; CDCl$_3$; chemical shifts δ in ppm; coupling constants J in Hz): 1.29 [mt, 12H: —C(CH$_3$)$_3$ and —CH$_3$ at position 16 or at position 17]; 1.35 (s, 3H: —CH$_3$ at position 16 or at position 17); 1.43 (mt, 1H: —H at position 7); 1.70 and 2.27 (2 dd, respectively J=6.5 and 5.5 and J=10 and 5.5, 1H each:—CH$_2$13 19); 1.87 (s, 1H: —OH at position 1); 1.92 (s, 3H: —CH$_3$); 2.13 and 2.50 (respectively broad d and dt, J=16 and J=16 and 4, 1H each: —CH$_2$— at position 6); 2.27 and 2.40 (2 mts, 1H each: —CH$_2$— at position 14); 2.40 (s, 3H: —COCH$_3$); 3.27 (mt, 1H: —OH at position 2'); 4.05 and 4.33 (2 d, J=9, 1H each: —CH$_2$— at position 20); 4.15 (d, J=7.5, 1H: —H at position 3); 4.63 (mt, 1H: —H at position 2'); 4.76 (d, J=4, 1H: —H at position 5); 5.29 (broad d, J=10, 1H: —H at position 3'); 5.36 (d, J=10, 1H: —CONH—); 5.72 (d, J=7.5, 1H: —H at position 2); 6.30 (broad t, J=8.5, 1H: —H at position 13); 6.52 (s, 1H: —H at position 10); 6.79 (d, J=1.5, 1H: —OCOC$_4$H$_3$O (—H at position 4)]; from 7.25 to 7.45 (mt, 5H: —C$_6$H$_5$ at position 3'); 7.48 (broad t, J=1.5, 1H: —OCOC$_4$H$_3$O (—H at positon 3 and H at position 5)]; 7.63 [(t, J=7.5, 1H: —OCOC$_6$H$_5$ (—H at position 4)]; 8.09 [broad s, 1H: —OCOC$_4$H$_3$O (—H at position 2)]; 8.17 [d, J=7.5,2H: —OCOC$_6$H$_5$ (—H at position 2 and H— at position 6)].

EXAMPLE 15

Working as in Example 1, but starting from 300 mg of 4α-acetoxy-2α-benzoyloxy-1β,10β-dihydroxy-5β,20-epoxy-7β,8β-methylene-9-oxo-19-nor-11-taxen-13α-yl (2R, 4S, 5R)-3-tert-butoxycarbonyl-2-(4-methoxy-phenyl)-4-phenyl-1,3-oxazolidine-5-carboxylate and 50 mg of 4-pyridinecarboxylic acid, 296 mg of 4α-acetoxy-2α-benzoyloxy-5β,20-epoxy-1β-hydroxy-7β,8β-methylene-9-oxo-10β-(4-pyridylcarbonyl)oxy-19-nor-11-taxen-13α-yl (2R, 4S, 5R)-3-tert-butoxycarbonyl-2-(4methoxyphenyl)-4phenyl-1,3-oxazolidine-5-carboxylate are obtained in the form of a white foam.

Working as in Example 1, but starting from 296 mg of 4α-acetoxy-2α-benzoyloxy-5β,20-epoxy-1β-hydroxy-7β,8β-methylene-9-oxo-10β-(4-pyridyl-carbonyl)oxy-19-nor-11-taxen-13α-yl (2R, 4S, 5R)-3-tert-butoxycarbonyl-2-(4-methoxyphenyl)-4-phenyl-1,3-oxazolidine-5-carboxylate, 159 mg of 4α-acetoxy-2α-benzoyloxy-5β,20-epoxy-1β-hydroxy-7β,8β-methylene-9-oxo-10β-(3-pyridylcarbonyl)

oxy-19-nor-11-taken-13α-yl (2R, 3S)-3-tert-butoxycarbonylamino-2-hydroxy-3-phenyl-priopionate are obtained in the form of a white foam, the characteristics of which are as follows:

optical rotation: $[\alpha]^{D}_{o}=-23$ (c=0.5; methanol)

$^1$H NMR spectrum (300 MHz; CDCl$_3$; chemical shifts δ in ppm; coupling constants J in Hz): 1.27 [(s, 9H: —C(CH$_3$)$_3$]; 1.32 (s, 3H: —CH$_3$ at position 16 or at position 17); 1.39 (s, 3H; —CH$_3$ at position 16 or at position 17); 1.42 (mt, 1H: —H at position 7); 1.70 and 2.27 (respectively dd and mt, J=6 and 5.5, 1H each: —CH$_2$— at position 19); 1.90 (s, 3H: —CH$_3$); 1.91 (s, 1H: —OH at position 1); 2.13 and 2.50 (respectively broad d and dt, J=16 J=16 and 4, 1H each: —CH$_2$— at position 6); 2.27 and 2.40 (2 mts, 1H each: —CH$_2$— at position 14); 2.40 (s, 3H: —COCH$_3$); 3.27 (mt, 1H: —OH at position 2'); 4.04 and 4.32 (2 d, J=9, 1H each: —CH$_2$— at position 20); 4.13 (d, J=7.5, 1H: —H at position 3); 4.63 (mt, 1H: —H at position 2'); 4.76 (d, J=4, 1H: —H at position 5); 5.27 (broad d, J=10z, 1H: —H at position 3'); 5.33 (d, J=10, 1H: —CONH—); 5.72 (d, J=7.5, 1H: —H at position 2); 6.29 (broad t, J=8.5, 1H: —H at position 13); 6.58 (s, 1H: —H at position 10); 7.25 to 7.45 (mt, 5H: —C$_6$H$_5$ at position 3 and H at position 5)]; 7.63 [(t, J=7.5, 1H: —OCOC$_6$H$_5$ (—H at position 4)]; 7.88 [(dd, J=6 and 1.5, 2H: —OCOC$_5$H$_4$N (—H at position 3 and —H at position 5)]; 8.17 [(d, J=6)]; 8.82 [(dd, J=6 and 1.5, 2H: —OCOC$_5$H$_4$N (—H at position 2 and —H at position 6)].

The new products of general formula (I) in which Z represents a radical of general formula (II) manifest significant inhibitory activity with respect to abnormal cell proliferation, and possess therapeutic properties permitting the treatment of patients having pathological conditions associated with abnormal cell proliferation. The pathological conditions include the abnormal cell proliferation of malignant or non-malignant cells of various issues and/or organs, comprising, without implied limitation, muscle, bone or connective tissue, the skin, brain, lungs, sex organs, the lymphatic or renal systems, mammary or blood cells, liver, the digestive system, pancreas and thyroid or adrenal glands. These pathological conditions can also include psoriasis, solid tumours, cancers of the ovary, breast, brain, prostate, colon, stomach, kidney or testicles, Kaposi's sarcoma, cholangiocarcinoma, choriocarcinoma, neuroblastoma, Wilms' tumour, Hodgkin's disease, melanoma, multiple myeloma, chronic lymphocytic leukaemia and acute or chronic granulocytic lymphoma. The new products according to the invention are especially useful for the treatment of cancel of the ovary. The products according to the invention may be used to prevent or delay the appearance or reappearance of the pathological conditions, or to treat these pathological conditions.

The products according to the invention may be administered to a patient according to different dosage forms suited to the chosen administration route, which is preferably the parenteral route. Parenteral administration comprises intravenous, intraperitoneal, intramuscular or subcutaneous administration. Intraperitoneal or intravenous administration is more especially preferred.

The present invention also comprises pharmaceutical compositions containing at least one product of general formula (I) in which Z represents a radical of general formula (II), in a sufficient amount suitable for use in human or veterinary therapy. The compositions may be prepared according to the customary methods, using one or more pharmaceutically acceptable adjuvants, vehicles or excipients. Suitable vehicles include diluents, sterile aqueous media and various non-=toxic solvents. Preferably, the compositions take the form of aqueous solutions or suspensions, injectable solutions which can contain emulsifying agents, colourings, preservatives or stabilizers.

The choice of adjuvants or excipients may be determined by the solubility and the chemical properties of the product, the particular mode of administration and good pharmaceutical practice.

For parenteral administration, sterile, aqueous or non-aqueous solutions or suspensions are used. For the preparation of non-aqueous solutions or suspensions, natural vegetable oils such as olive oil, sesame oil or liquid petroleum, or injectable organic esters such as ethyl oleate, may be used. The sterile aqueous solutions can consist of a solution of a pharmaceutically acceptable salt dissolved in water. The aqueous solutions are suitable for intravenous administration provided the pH is appropriately adjusted and the solution is made isotonic, for example with a sufficient amount of sodium chloride or glucose. The sterilization may be carried out by heating or by any other means which does not adversely affect the composition.

It is clearly understood that all the products participating in the compositions according to the invention must be pure and non-toxic in the amounts used.

The compositions can contain at least 0.01% of therapeutically active product. The amount of active product in a composition is such that a suitable dosage can be prescribed. Preferably, the compositions are prepared in such a way that a single dose contains from 0.01 to 1000 mg approximately of active product for parenteral administration.

The therapeutic treatment may be performed concurrently with other therapeutic treatments including antineoplastic drugs, monoclonal antibodies, immunotherapy or radiotherapy or biological response modifiers. The response modifiers include, without implied limitation, lymphokines and cytokines such as interleukins, interferons (α, β or δ) and TNF. Other chemotherapeutic agents which are useful in the treatment of disorders due to abnormal cell proliferation include, without implied limitation, alkylating agents, for instance nitrogen mustards such as mechlorethamine, cyclophosphamide, melphalan and chlorambucil, alkyl sulphonates such as busulfan, nitrosoureas such as carmustine, lomustine, semustine and streptozocin, triazenes such as dacarbazine, antimetabolites such as folic acid analogues, for instance methotrexate, pyrimidine analogues such as fluorouracil and cytarabine, purine analogues such as mercaptopurine and thioguanine, natural products, for instance vinca alkaloids such as vinblastine, vincristine and vindesine, epipodophyllotoxins such as etoposide and teniposide, antiboiotics such as dactinomycin, daunorubicin, doxorubicin, bleomycin, plicamycin and mitomycin, enzymes such as L-asparaginase, various agents such as coordination complexes of platinum, for instance cisplatin, substituted ureas such as hydroxyurea, methylhydrazine derivatives such as procarbazine, adrenocortical suppressants such as mitotane and aminoglutethimide, hormones and antagonists such as adrenocortiocosteriods such as prednisone, progestins such as hydroxyprogesterone caproate, methoxyprogesterone acetate and megestrol acetate, oestrogens such as diethylstilboestrol and ethynyloestradiol, antioestrogens such as tamoxifen, and androgens such as testosterone propionate and fluoxymesterone.

The doeses used for carrying out the methods according to the invention are those whic permit a prophylactic treatment or a maximum therapeutic response. The doses vary according to the administration form, the particular product selected and features distinctive to the subject to be treated. In general, the doses are those which are therapeutically effective for the treatment of disorders due to abnormal cell proliferation. The products according to the invention may be administered as often as necessary to obtain the desired therapeutic effect. Some patients may respond rapidly to relatively high or low doses, and then require low or zero maintenance doses. Generally, low doses will be used at the beginning of the treatment and, if necessary, increasingly stronger doses will be administered until an optimum effect is obtained. For other patients, it may be necessary to administer maintenance doses 1 to 8 times a day, and preferably 1 to 4 times, according to the physiological requirements of the patient in question. It is also possible that some patients may require the use of only one to two daily administrations.

In man, the doses are generally between 0.01 and 200 mg/kg. For intraperitoneal administration, the doses will generally be between 0.1 and 100 mg/kg, preferably between 0.5 and 50 mg/kg and still more specifically between 1 and 10 mg/kg. For intravenous administration, the doses are generally between 0.1 and 50 mg/kg, preferably between 1 and 5 mg/kg and still more specifically between 1 and 2 mg/kg. It is understood that, in order to choose the most suitable dosage, account should be taken of the administration route, the patient's weight, general state of health and age and all factors which may influence the efficacy of the treatment.

The example which follows illustrates a composition according to the invention.

EXAMPLE 40 mg of the product obtained in Example 1 are dissolved in 1 cm³ of Emulphor EL 620 and 1 cm³ of ethanol, and the solution is then diluted by adding 18 cm³ of physiological saline.

The composition is administered by perfusion over 1 hour by introduction in physiological solution.

We claim:

1. A taxoid of general formula:

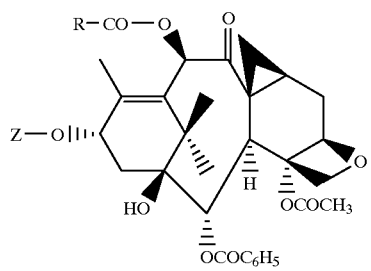

(I)

in which:

R represents a substituted alkenyl radical containing 2 to 8 carbon atoms in an unbranched or branched chain, an unsubstituted or substituted alkynyl radical containing 2 to 8 carbon atoms in an unbranched or branched chain, an unsubstituted or substituted cycloalkyl radical containing 3 to 6 carbon atoms or an unsubstituted or substituted cycloalkenyl radical containing 3 to 6 carbon atoms, said substituted radicals being substituted with a halogen atom selected from fluorine, chlorine, bromine and iodine atoms or with an amino radical, an alkylamino radical in which the alkyl portion contains 1 to 4 carbon atoms, a dialkylamino radical in which each alkyl portion contains 1 to 4 carbon atoms or, with the nitrogen atom to which it is linked, forms a saturated 5- or 6-membered heterocyclic radical which may contain a second hetero atom selected from oxygen, sulphur and nitrogen atoms, wherein said heterocyclic radical is unsubstituted or substituted with an alkyl radical containing 1 to 4 carbon atoms, a phenyl radical or a phenylalkyl radical in which the alkyl portion contains 1 to 4 carbon atoms, a carboxyl radical, an alkyloxycarbonyl radical in which the alkyl portion contains 1 to 4 carbon atoms, a cyano radical, a carbamoyl radical, an N-alkylcarbamoyl radical in which the alkyl portion contains 1 to 4 carbon atoms, an N,N-dialkyl-carbamoyl radical in which each alkyl portion contains 1 to 4 carbon atoms, or, with the nitrogen atom to which it is linked, forms a saturated 5- or 6-membered heterocyclic radical which may contain a second hetero atom selected from oxygen, sulphur and nitrogen atoms, wherein such heterocyclic radical is unsubstituted or substituted with an alkyl radical containing 1 to 4 carbon atoms, a phenyl radical, or a phenylalkyl radical in which the alkyl portion contains 1 to 4 carbon atoms; or a 5- or 6-membered aromatic heterocyclic radical containing an oxygen, sulphur or nitrogen atom as a hetero atom, and Z represents a hydrogen atom or a radical of general formula:

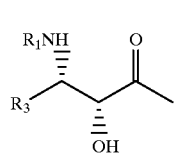

(II)

in which:

R$_1$ represents a benzoyl radical unsubstituted or substituted with one or more identical or different atoms or radicals selected from halogen atoms, alkyl radicals containing 1 to 4 carbon atoms, alkoxy radicals containing 1 to 4 carbon atoms, and trifluoromethyl radicals, a thenoyl radical, a furoyl radical, or a radical R$_2$—O—CO— in which:

R$_2$ represents an alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms, or a bicycloalkyl radical containing 7 to 10 carbon atoms, these radicals being unsubstituted or substituted with one or more substituents selected from halogen atoms, hydroxyl radicals, alkoxy radicals containing 1 to 4 carbon atoms, dialkylamino radicals in which each alkyl portion contains 1 to 4 carbon atoms, piperidino or morpholino radicals, 1-piperazinyl radicals unsubstituted or substituted at position 4 with an alkyl radical containing 1 to 4 carbon atoms or with a phenylalkyl radical in which the alkyl portion contains 1 to 4 carbon atoms, cycloalkyl radicals containing 3 to 6 carbon atoms, cycloalkenyl radicals containing 4 to 6 carbon atoms, phenyl radicals unsubstituted or substituted with one or more atoms or radicals selected from halogen atoms, alkyl radicals containing 1 to 4 carbon atoms, alkoxy radicals containing 1 to 4 carbon atoms, cyano radicals, carboxyl radicals, and alkoxycarbonyl radicals in which the alkyl portion contains 1 to 4 carbon atoms;

a phenyl or α- or β-naphthyl radical unsubstituted or substituted with one or more atoms of radicals selected from halogen atoms, alkyl radicals containing 1 to 4 carbon atoms, alkoxy radicals containing 1 to 4 carbon atoms, a 5-membered aromatic heterocyclic radical; and a saturated heterocyclic radical containing 4 to 6 carbon atoms, unsubstituted or substituted with one or more alkyl radicals containing 1 to 4 carbon atoms;

$R_3$ represents an unbranched or branched alkyl radical containing 1 to 8 carbon atoms, an unbranched or branched alkenyl radical containing 2 to 8 carbon atoms, an unbranched or branched alkenyl radical containing 2 to 8 carbon atoms, a cycloalkyl radical containing 3 to 6 carbon atoms, a phenyl or α- or β-naphthyl radical unsubsituted or substituted with one or more atoms or radicals selected from halogen atoms, alkyl, alkenyl, alkenyl, aryl, aralkyl, alkoxy, alkylthio, aryloxy, arylthio, hydroxyl, hydroxyalkyl, mercapto, formyl, acyl, acylamino, aroylamino, alkoxy carbonylamino, amino, alkylamino, dialkylamino, carboxyl, alkoxycarbonyl, carbamoyl, alkylcarbamoyl, dialkylcarbamoyl, cyano, nitro and trifloromethyl radicals, or a 5-membered aromatic heterocycle containing one or more identical or different hetero atoms chosen from nitrogen, oxygen and sulphur atoms and unsubstituted or substituted with one or more identical or different substituents selected from halogen atoms, alkyl, alkoxy, aryl, aryloxy, amino, alkylamino, dialkylamino, acylamino, alkoxycarbonylamino, acyl, arylcarbonyl, cyano, carboxyl, carbamoyl, alkylcarbamoyl, dialkylcarbamoyl or alkoxycarbonyl radicals, wherein the substituents of the phenyl, α- or β-naphthyl and aromatic heterocyclic radicals, the alkyl radicals and the alkyl portions of the other radicals contain 1 to 4 carbon atoms, the alkenyl and alkenyl radicals contain 2 to 8 carbon atoms, and the aryl radicals are phenyl or α- or β-naphthyl radicals.

2. The taxoid according to claim 1 in which Z represents a hydrogen atom or a radical of general formula (II) in which $R_1$ represents a benzoyl radical or a radical $R_2$—O—CO— in which $R_2$ represents a tert-butyl radical;

$R_3$ represents an alkyl radical containing 1 to 6 carbon atoms, an alkenyl radical containing 2 to 6 carbon atoms, a cycloalkyl radical containing 3 to 6 carbon atoms, a phenyl radical unsubstituted or substituted with one or more identical or different atoms or radicals selected from halogen atoms, alkyl, alkoxy, dialkylamino, acylamino, alkoxycarbonylamino, trifluoromethyl, 2- or 3-furyl, 2- or 3-thienyl, and 2-, 4- or 5-thiazolyl radicals; and R represents a cycloalkyl radical containing 3 to 6 carbon atoms, a 2-, 3- or 4-pyridyl radical, 2- or 3-furyl radical or 2- or 3-thienyl radical.

3. A taxoid according to claim 1 in which Z represents a hydrogen atom or a radical of general formula (II) in which $R_1$ represents a benzoyl radical or a radical $R_2$—O—CO— in which $R_2$ represents a tert-butyl radical;

$R_3$ represents an isobutyl, isobutenyl, butenyl, cyclohexyl, phenyl, 2-furyl, 3-furyl, 2-thienyl, 3-thienyl, 2-thiazolyl, 4-thiazolyl or 5-thiazolyl radical; and R represents a cyclopropyl, cyclopentyl, 2-pyridyl, 2-thienyl or 2-furyl radical.

4. A process for preparing a taxoid according to claim 1, comprising esterifying a product of general formula:

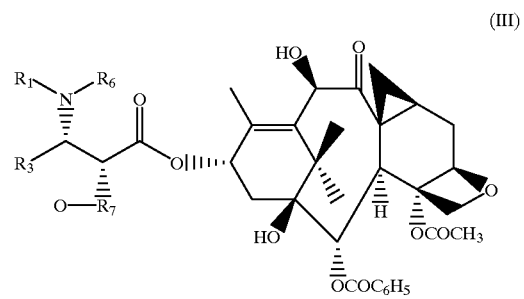

in which $R_1$ and $R_3$ are defined in claim 1, and either $R_6$ represents a hydrogen atom and $R_7$ represents a group protecting the hydroxyl function, or $R_8$ and $R_7$ together form a saturated 5- or 6-membered heterocycle, by means of an acid of general formula:

R—CO—OH    (IV)

in which R is defined in claim 1, or by means of a derivative of said acid to obtain a product of general formula:

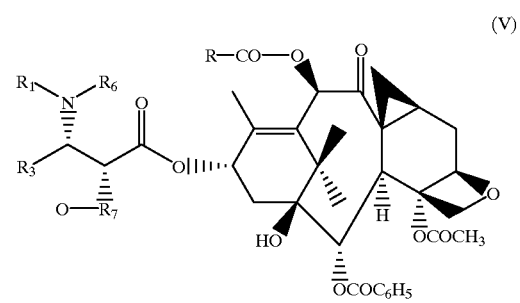

in which $R_1$, $R_3$, $R_6$ and $R_7$ are defined as above, followed by replacing the protective groups $R_7$ and $R_6$ and $R_7$ with hydrogen atoms.

5. The process according to claim 4, wherein the esterification is performed by means of an acid of general formula (IV) in the presence of a condensing agent and an activating agent in an organic solvent at a temperature of between −10 and 90° C.

6. The process according to claim 4, wherein the esterification is performed by means of an acid of general formula (IV) in the form of the symmetrical anhydride, working in the presence of an activating agent in an organic solvent at a temperature of between 0 and 90° C.

7. The process according to claim 4, wherein the esterification is performed by means of an acid of general formula (IV) in halide form or in the form of a mixed anhydride with an aliphatic or aromatic acid, optionally prepared in situ, in the presence of a base, working in an organic solvent at a temperature of between 0 and 80° C.

8. The process according to claim 4, wherein replacement of either or both of the protective groups $R_6$ and $R_7$ by hydrogen atoms is performed in the following manner:

1) when $R_6$ represents a hydrogen atom and $R_7$ represents a group protecting the hydroxyl function, the protective groups are replaced by hydrogen atoms by means of an inorganic or organic acid used alone or mixed, working in an organic solvent selected from alcohols, ethers, esters, aliphatic hydrocarbons, halogenated aliphatic hydrocarbons, aromatic hydrocarbons or nitriles at a temperature between −10 and 60° C.;

2) when $R_6$ and $R_7$ form an oxazolidine ring of general formula:

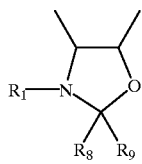

(VI)

in which $R_1$ is defined in claim 1 and $R_8$ and $R_9$, which may be identical or different, represent a hydrogen atom, an alkyl radical containing 1 to 4 carbon atoms, an aralkyl radical in which the alkyl portion contains 1 to 4 carbon atoms and the aryl portion is a phenyl radical optionally substituted with one or more alkoxy radicals containing 1 to 4 carbon atoms, or an aryl radical, or alternatively $R_8$ represents an alkoxy radical containing 1 to 4 carbon atoms, a trihalomethyl radical or a phenyl radical substituted with a trihalomethyl radical and $R_9$ represents a hydrogen atom, or alternatively $R_8$ and $R_9$, together with the carbon atom to which they are linked, form a 4- to 7-membered ring, the protective group formed by $R_6$ and $R_7$ is replaced by hydrogen atoms in the following manner:

a) when $R_1$ represents a tert-butoxycarbonyl radical and $R_8$ and $R_9$, which may be identical or different, represent an alkyl, aralkyl or aryl radical, or alternatively $R_8$ represents a trihalomethyl radical or a phenyl radical substituted with a trihalomethyl radical and $R_9$ represents a hydrogen atom, or alternatively $R_8$ and $R_9$ together form a 4- to 7-membered ring, the ester of general formula (V) is treated with an inorganic or organic acid, where appropriate in an organic solvent, to obtain a product of general formula:

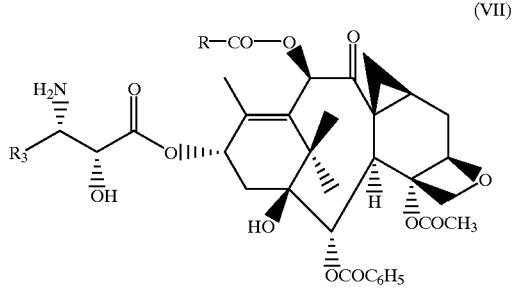

(VII)

in which R and $R_3$ are defined in claim 1, which is acylated by means of benzoyl chloride in which the phenyl ring is unsubstituted or substituted, by means of thenoyl chloride, by means of furoyl chloride or by means of a product of general formula $R_2$—O—$CO_X$ (VIII)

in which $R_2$ is defined as in claim 1 and X represents a halogen atom or a residue —O—$R_2$ or —O—CO—O—$R_2$, to obtain a product of general formula (I) in which Z represents a radical of general formula (II);

b) when $R_1$ represents an unsubstituted or substituted benzoyl radical, radical, or furoyl radical or a radical $R_2$O—CO— in which $R_2$ is defined as in claim 1, $R_8$ represents a hydrogen atom, an alkoxy radical containing 1 to 4 carbon atoms, or a phenyl radical substituted with one or more alkoxy radicals containing 1 to 4 carbon atoms and $R_9$ represents a hydrogen atom, replacement of the protective group formed by $R_6$ and $R_7$ by hydrogen atoms is performed in the presence of an inorganic or organic acid used alone or mixed in a stoichiometric or catalytic amount, working in an organic solvent at a temperature between −10 and 60° C.

9. A process for preparing a product of general formula (I) in which Z represents a radical of general formula (II), comprising esterifying a baccatin III derivative of formula:

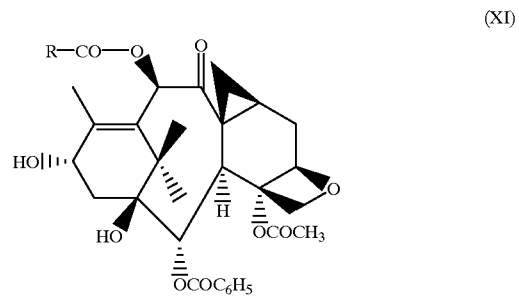

(XI)

wherein R is defined as in claim 1, by means of an acid of general formula:

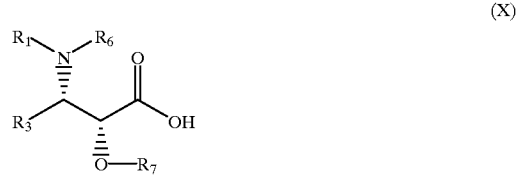

(X)

in which $R_1$ and $R_3$ are defined as in claim 1, and $R_6$ and $R_7$ are defined as in claim 4, or by means of a derivative of said acid, followed by replacement of the protective groups $R_7$, or $R_6$ and $R_7$, by hydrogen atoms.

10. The process according to claim 9, wherein the esterification is performed according to the process of claim 5.

11. The process according to claim 9, wherein the protective groups $R_7$, or $R_6$ and $R_7$, are replaced by hydrogen atoms according to the conditions of claim 8.

12. A process for preparing a taxoid according to claim 1 for which Z represents a hydrogen atom, comprising esterifying a product of formula:

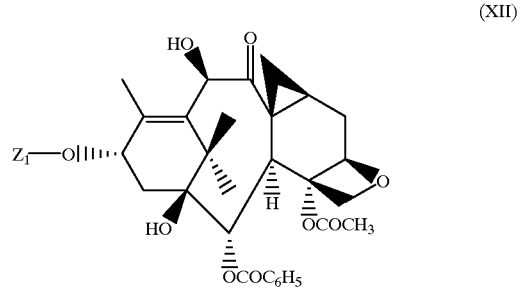

(XII)

in which $Z_1$ represents a group protecting the hydroxyl function, by means of an acid of general formula (IV) or of a derivative of said acid, and replacing the protective group $Z_1$ by a hydrogen atom under conditions which do not affect the remainder of the molecule.

13. A pharmaceutical composition, comprising at least one taxoid according to claim 1 in which Z represents a radical of general formula (II), in combination with one or more pharmaceutically acceptable products.

14. The taxoid according to claim 2, wherein in said substituted $R_3$ phenyl radical said halogen atom is selected from fluorine and chlorine, said alkyl radical is a methyl radical, said alkoxy radical is a methoxy radical, said dialkylamino radical is a dimethylamino radical, said acylamino radical is an acetylamino radical, and said alkoxycarbonylamino radical is a tert-butoxycarbonylamino radical.

15. The process according to claim 4, wherein said derivative of said acid of general formula (IV) is a halide, a symmetrical anhydride, or a mixed anhydride.

16. The process according to claim 8, wherein either or both of said $R_8$ and $R_9$ aryl radicals is a phenyl radical unsubstituted of substituted with one or more alkoxy radicals containing 1 to 4 carbon atoms.

17. The process according to claim 9, wherein said derivative of said acid of general formula (IV) is a halide, a symmetrical anhydride, or a mixed anhydride.

18. The process according to claim 12, wherein said derivative of said acid of general formula (IV) is a halide, a symmetrical anhydride, or a mixed anhydride.

19. The pharmaceutical composition according to claim 13, wherein said pharmaceutically acceptable product is pharmacologically active.

* * * * *

UNITED STATES PATENT AND TRADEMARK OFFICE
CERTIFICATE OF CORRECTION

PATENT NO.    : 5,959,125
DATED         : September 28, 1999
INVENTOR(S)   : Herve BOUCHARD et al.

It is certified that error appears in the above-identified patent and that said Letters Patent is hereby corrected as shown below:

Title Page, Item [57], in the Abstract, line 4, before "aromatic",
    insert --optionally--; and line 9, "heterocycl" should read --heterocyclyl--

Claim 1, col. 29, line 21, "unsubsituted" should read --unsubstituted--.
Claim 1, col. 29, line 28, "trifloromethyl" should read --trifluoromethyl--.
Claim 4, col. 30, line 21, "$R_8$ and $R_7$" should read --$R_6$ and $R_7$--.
Claim 4, col. 30, line 43, "$R_7$ and $R_6$ and $R_7$" should read --$R_7$ or $R_6$ and $R_7$--.
Claim 8, col. 31, line 60, "$R_2-O-CO_X$" should read --$R_2-O-CO-X$--.
Claim 8, col. 31, line 67, before "radical" (second occurrence), insert --thenoyl--.
Claim 16, col. 34, line 3, after "unsubstituted", "of" should read --or--.

Signed and Sealed this

Fifteenth Day of May, 2001

Attest:

NICHOLAS P. GODICI

*Attesting Officer*    *Acting Director of the United States Patent and Trademark Office*